United States Patent [19]

Jacobs et al.

[11] Patent Number: 5,521,199

[45] Date of Patent: May 28, 1996

[54] PIPERIDINYL COMPOUNDS AS NEUROKININ RECEPTOR ANTAGONISTS

[75] Inventors: Robert T. Jacobs, Macclesfield, England; Ashokkumar B. Shenvi, Wilmington, Del.

[73] Assignee: Zeneca Limited, London, United Kingdom

[21] Appl. No.: 242,949

[22] Filed: May 16, 1994

[30] Foreign Application Priority Data

May 17, 1993 [GB] United Kingdom .................. 9310066

[51] Int. Cl.$^6$ ...................... A61K 31/445; C07D 211/26
[52] U.S. Cl. ........................................... 514/331; 546/233
[58] Field of Search .............................. 546/233; 514/331

[56] References Cited

U.S. PATENT DOCUMENTS

| | | | |
|---|---|---|---|
| 5,236,921 | 8/1993 | Emonds-Alt et al. | 514/252 |
| 5,300,648 | 4/1994 | Emonds-Alt | 346/193 |
| 5,350,852 | 9/1994 | Emonds-Alt | 544/336 |

FOREIGN PATENT DOCUMENTS

| | | |
|---|---|---|
| 2029275 | 5/1991 | Canada . |
| 2067924 | 11/1992 | Canada . |
| 2090785 | 9/1993 | Canada . |
| 0428434 | 5/1991 | European Pat. Off. . |
| 0474561 | 3/1992 | European Pat. Off. . |
| 0512902 | 11/1992 | European Pat. Off. . |
| 0515240 | 11/1992 | European Pat. Off. . |
| 0512901 | 11/1992 | European Pat. Off. . |
| 0559538 | 9/1993 | European Pat. Off. . |
| 923177 | 1/1993 | South Africa . |
| 923178 | 1/1993 | South Africa . |
| WO94/10146 | 5/1994 | WIPO . |

OTHER PUBLICATIONS

A. Graham et al., "Isolation and Characterisation of the Human Lung NK-2 Receptor Gene Using Rapid Amplification of cDNA Ends", *Biochemical and Biophysical Research Communications*, (1991), vol. 177, No. 1, 8–16.

X. Emonds–Alt et al., "Pharmacological Profile and Chemical Synthesis of SR 48968, a Non–Peptide Antagonist of the Neurokinin A ($NK_2$) Receptor", *Biorganic & Medicinal Chemistry Letters*, (1993), vol. 3, No. 5, 925–930.

D. Aharony et al., "Pharmacologic Characterization of the Novel Ligand [4,5-$^3$H-LEU$^9$]Neurokinin-A Binding to NK-2 Receptors on Hamster Urinary Bladder Membranes", *Neuropeptides*, (1992), 23, 121–130.

M. Needham et al., "LCR/MEL: A Versatile System for High-Level Expression of Heterologous Proteins in Erythroid Cells", *Nucleic Acids Research*, (1992), vol. 20, No. 5, 997'1003.

Primary Examiner—Ceila Chang
Attorney, Agent, or Firm—Robert J. Harris

[57] ABSTRACT

The present invention concerns the novel alkyl substituted heterocycles of formula I, set out below, wherein Q, $Q^1$, $Q^2$ and R have the values defined herein, which antagonize the pharmacological actions of one of the endogenous neuropeptide tachykinins at the neurokinin 2 ($NK^2$) receptor making them useful whenever such antagonism is desired, such as in the treatment of asthma and related conditions. The invention also provides pharmaceutical compositions containing the alkyl substituted heterocycles for use in such treatment, methods for their use, and processes and novel intermediates for their manufacture.

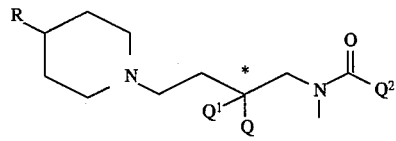

8 Claims, 3 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear     ( i x ) SEQUENCE DESCRIPTION: SEQ ID NO:1

GCGCAAGCTT ATGGG　　　　　　　　　　　　　　　　15

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( i x ) SEQUENCE DESCRIPTION: SEQ ID NO:2:

GTCCCCATAA GCTTGCGC　　　　　　　　　　　　　　18

PIPERIDINYL COMPOUNDS AS NEUROKININ RECEPTOR ANTAGONISTS

This invention concerns novel alkyl substituted heterocycles, and, more particularly, novel substituted piperidine derivatives which antagonize the pharmacological actions of one or more of the endogenous neuropeptide tachykinins known as neurokinins, particularly at the neurokinin 2 (NK2) receptor. The novel alkyl substituted heterocycles are useful whenever such antagonism is desired. Thus, such compounds may be of value in the treatment of those diseases in which an NK2 receptor is implicated, for example, in the treatment of asthma and related conditions. The invention also provides pharmaceutical compositions containing the novel alkyl substituted heterocycles for use in such treatment, methods for their use, and processes and intermediates for the manufacture of the novel alkyl substituted heterocycles.

The mammalian neurokinins comprise a class of peptide neurotransmitters which are found in the peripheral and central nervous systems. The three principal neurokinins are Substance P (SP), Neurokinin A (NKA) and Neurokinin B (NKB). There are also N-terminally extended forms of at least NKA. At least three receptor types are known for the three principal neurokinins. Based upon their relative selectivities favoring the neurokinin agonists SP, NKA and NKB, respectively, the receptors are classified as neurokinin 1 (NK1), neurokinin 2 (NK2) and neurokinin 3 (NK3) receptors, respectively. In the periphery, SP and NKA are localized in C-afferent sensory neurons, which neurons are characterized by non-myelinated nerve endings known as C-fibers, and are released by selective depolarization of these neurons, or selective stimulation of the C-fibers. C-Fibers are located in the airway epithelium, and the tachykinins are known to cause profound effects which clearly parallel many of the symptoms observed in asthmatics. The effects of release or introduction of tachykinins in mammalian airways include bronchoconstriction, increased microvascular permeability, vasodilation and activation of mast cells. Thus, the tachykinins are implicated in the pathophysiology and the airway hyperresponsiveness observed in asthmatics; and blockade of the action of released tachykinins may be useful in the treatment of asthma and related conditions. Peptidic NK2 antagonists have been reported. For example, a cyclic hexapeptide known as L-659,877 has been reported as a selective NK2 antagonist. Nonpeptidic NK2 antagonists also have been reported, for example in European Patent Application, Publication Number (EPA) 428434, EPA 474561, EPA 512901, EPA 512902 and EPA 515240, as well as in EPA 559538. We have discovered a series of nonpeptidic NK2 antagonists, and this is the basis for our invention.

According to the invention, there is provided a Compound of the invention which is a compound of formula I (formula set out hereinbelow following the Examples, together with other formulae denoted by Roman numerals) wherein Q is phenyl which may bear one or two substituents independently selected from halo, trifluoromethyl, hydroxy, (1–3C)alkoxy, (1–3C)alkyl and methylenedioxy; or Q is thienyl, imidazolyl, benzo[b]thiophenyl or naphthyl any of which may bear a halo substituent; or Q is biphenylyl; or Q is carbon-linked indolyl which may bear a benzyl substituent at the 1-position;

$Q^1$ is hydrogen or (1–3C)alkyl;

$Q^2$ is aryl or heteroaryl, which aryl or heteroaryl radical may bear one or more substituents independently selected from halo, hydroxy, (1–4C)alkoxy or (1–4C)alkyl;

R is (1–8C)alkyl or (3–8C)cycloalkyl which may bear one or more substituents selected from the group consisting of halo, (3–6C)cycloalkyl, cyano, nitro, hydroxy, lower alkoxy, lower acyloxy, aroyl, heteroaroyl, oxo, imino (which may bear a (1–6C)alkyl, (3–6C)cycloalkyl, (1–5C)acyl or aroyl substituent) hydroxyimino (which hydroxyimino may bear a lower alkyl or a phenyl substituent on the oxygen), an amino group of formula $NR^A R^B$, an amino group of formula $NR^C R^D$, an amidino group of formula $C(=NR^G)NR^E R^F$, and a carbamoyl group of formula $CON(OR^K)R^L$, but excluding any compound wherein a hydroxy and an oxo substituent together form a carboxy group, wherein An amino group of formula $NR^A R^B$ contains zero to about seven carbon atoms and each of $R^A$ and $R^B$ is independently hydrogen, (1–5C)alkyl or (3–6C)cycloalkyl, or $R^A$ and $R^B$ together with the nitrogen to which they are attached form a pyrrolidino, piperidino, morpholino, thiomorpholino (or its S-oxide) or piperazinyl group (which piperazinyl group may bear a methyl or ethyl group at the 4-position); and wherein $R^C$ is hydrogen or lower alkyl and $R^D$ is lower acyl, aroyl or heteroaroyl; or $R^D$ is a group of formula $C(=J)NR^E R^F$ in which J is oxygen, sulfur, $NR^G$ or $CHR^H$; and wherein the amino group $NR^E R^F$ contains zero to about seven carbon atoms and each of $R^E$ and $R^F$ is independently hydrogen, (1–5C)alkyl or (3–6C)cycloalkyl, or $NR^E R^F$ together with the nitrogen to which they are attached form a pyrrolidino, piperidino, morpholino, thiomorpholino (or its S-oxide) or piperazinyl group (which piperazinyl group may bear a methyl or ethyl group at the 4-position) or $R^E$ is hydrogen or lower alkyl and $R^F$ together with $R^G$ forms an ethylene or trimethylene group; $R^G$ is hydrogen, lower alkyl or together with $R^F$ forms an ethylene or trimethylene group; $R^H$ is cyano nitro or $SO_2 R^J$ and $R^J$ is lower alkyl or phenyl; $R^K$ and $R^L$ are independently (1–3C)alkyl; and in which a cyclic group which is a substituent on R or formed by substitution on R may bear one or more (1–3C)alkyl groups on carbon as further substituents; and in which any aryl or heteroaryl group which is a part of the group R may bear one or more halo, lower alkyl, lower alkoxy, cyano, trifluoromethyl or nitro substituents;

or a pharmaceutically acceptable salt thereof.

A particular subgroup of the invention is one in which Q is 3,4-dichlorophenyl, $Q^1$ is hydrogen and $Q^2$ is phenyl, or a pharmaceutically acceptable salt thereof.

It will be appreciated that a compounds of formula I contains one or more asymmetrically substituted carbon atoms such that such compounds may be isolated in optically active, racemic and/or diastereomeric forms. Some compounds may exhibit polymorphism. It is to be understood that the present invention encompasses any racemic, optically-active, diastereomeric, polymorphic or stereoisomeric form, or mixtures thereof, which form possesses NK2 antagonist properties, it being well known in the art how to prepare optically-active forms (for example, by resolution of the racemic form or by synthesis from optically-active starting materials) and how to determine the NK2 antagonist properties by the standard tests described hereinafter. It may be preferred to use the compound of formula I in a form which is characterized as containing, for example, at least 95%, 98% or 99% enantiomeric excess of the form which corresponds to the (S)-configuration at the center indicated by * in formula I when Q is 3,4-dichlorophenyl, $Q^1$ is hydrogen and $Q^2$ is phenyl.

In this specification R, $R^A$, $R^B$, et cetera stand for generic radicals and have no other significance. It is to be understood that the generic term "(1–8C)alkyl" includes both straight and branched chain alkyl radicals but references to individual alkyl radicals such as "propyl" embrace only the straight chain ("normal") radical, branched chain isomers such as "isopropyl" being referred to specifically. A similar convention applies to other generic groups, for example, alkoxy, alkanoyl, et cetera. Halo is fluoro, chloro, bromo or iodo. Lower alkyl and lower alkoxy refer to radicals containing one to about four carbon atoms. Lower acyl and lower acyloxy refer to radicals containing one to about five carbon atoms. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms selected from the group consisting of oxygen, sulfur and nitrogen, as well as a radical of an ortho-fused bicyclic heterocycle of about eight to ten ring atoms derived therefrom, particularly a benz-derivative or one derived by fusing a propenylene, trimethylene or tetramethylene diradical thereto, as well as a stable N-oxide thereof. Aroyl and heteroaroyl refer to arylcarbonyl and heteroarylcarbonyl radicals, respectively.

A pharmaceutically acceptable salt is one made with an acid which provides a physiologically acceptable anion.

Particular values are listed below for radicals, substituents and ranges for illustration only and they do not exclude other defined values or other values within defined ranges for the radicals and substituents. A particular value for Q is 3,4-dichlorophenyl, for $Q^1$ is hydrogen, and for $Q^2$ is phenyl. Particular values for (1–8C)alkyl include ethyl, propyl, butyl, pentyl, isopropyl, 3-pentyl and 4-heptyl. Particular values for a substituent on the (1–8C)alkyl group of R include hydroxy, acetoxy, oxo, hydroxyimino, methoxyimino, propylamino and acetamido. A particular value for two concurrent substituents on R is an oxo substituent, together on the same carbon with an amino group of formula $NR^AR^B$, thereby forming a carbamoyl group, for example an N-propylcarbamoyl group. Particular values for R include 1-hydroxyethyl, 1-hydroxypropyl, 1-hydroxybutyl, 1-hydroxy-1-methylethyl, 1-ethyl-1-hydroxy-propyl, 1-hydroxy-1-propylbutyl, 2-hydroxyethyl, acetyl, propionyl, 1-hydroxyiminoethyl, 1-hydroxyiminopropyl, 1-methoxyiminoethyl, 1-methoxyiminopropyl, 2-acetoxyethyl and 2-acetamidoethyl.

Specific compounds of formula I are described in the accompanying Examples. The compound of Example 16 is a preferred embodiment of the invention.

Pharmaceutically acceptable salts of a compound of formula I include those made with a strong inorganic or organic acid which affords a physiologically acceptable anion, such as, for example, hydrochloric, sulfuric, phosphoric, methanesulfonic, or para-toluenesulfonic acid.

A compound of formula I may be made by processes which include processes known in the chemical art for the production of structurally analogous heterocyclic compounds. Such processes and intermediates for the manufacture of a compound of formula I as defined above are provided as further features of the invention and are illustrated by the following procedures in which the meanings of generic radicals are as defined above unless otherwise indicated:

(a) Alkylating a corresponding piperidine of formula II with an aldehyde of formula III, by reductive alkylation, or with an alkylating agent of formula IV in which Y is a leaving group. The alkylation is preferably carried out by a conventional reductive alkylation, for example as described in Example 1, by the in situ, acid-catalyzed formation of an imminum salt, followed by reduction with sodium cyanoborohydride in alcoholic solvent. The reductive alkylation may be carried out in a suitable solvent, such as methanol, tetrahydrofuran or acidic water, using a suitable reducing agent, such as for example sodium cyanoborohydride, conveniently at a temperature in the range of –20° to 50° C., preferably in the range of 0° to 25° C.

(b) For a compound of formula I which is a ketone in which R bears an oxo substituent, condensation of a corresponding compound of formula V in which $R^1$ contains an N,N-disubstituted carbamoyl group, such as for example an N-methyl-N-methoxy carbamoyl group, with the required organomagnesium or organolithium reagent, such as for example an organomagnesium chloride or bromide (Grignard reagent). A Grignard addition may be carried out in a suitable solvent, such as for example diethyl ether or tetrahydrofuran, conveniently at a temperature in the range of –20° to 50° C., preferably in the range of 0° to 25° C. Suitable conditions for carrying out a Grignard addition can be found at Example 3.

(c) For a compound of formula I wherein R is a primary or secondary hydroxy, reduction of a corresponding compound of formula I wherein R is oxo, using a conventional reducing agent which does not reduce the benzamide moiety. Conveniently, the reduction may be carried out using sodium borohydride in a suitable solvent, such as for example methanol or ethanol, at a temperature in the range of –20 to 50° C., preferably in the range of 0° to 25° C. Suitable conditions for carrying out the reduction can be found at Example 4.

(d) For a compound of formula I wherein R is hydroxyimino (or an oxygen-substituted hydroxyimino), by condensation of a corresponding compound of formula I wherein R is oxo with hydroxylamine (or the corresponding oxygen-substituted hydroxylamine), conveniently as its hydrochloride salt. The condensation may be carried out in a suitable solvent, such as for example methanol or ethanol, and in the presence of a suitable base, such as for example pyridine. The reaction may conveniently be carried out at a temperature in the range of 0° to 100° C., preferably at a temperature in the range of 25° to 75° C. Suitable conditions for carrying out the condensation can be found at Example 5 or 6.

Whereafter, when it is desired to use a protecting group during all or a portion of an above described process; the protecting group then is removed when the final compound is to be formed.

Whereafter, for any of the above procedures, when a pharmaceutically acceptable salt of a compound of formula I is required, it may be obtained by reacting the compound of formula I with an acid affording a physiologically acceptable counterion or by any other conventional procedure.

If not commercially available, the necessary starting materials for the above procedures may be made by procedures which are selected from standard techniques of heterocyclic chemistry, techniques which are analogous to the synthesis of known, structurally similar compounds, and techniques which are analogous to the above described procedures or the procedures described in the Examples. The starting materials and the procedures for their preparation are additional aspects of the invention.

As will be clear to one skilled in the art, a variety of sequences is available for preparation of the starting materials, and the sequences leading to the starting materials and products of the invention may be altered if appropriate considerations regarding the synthetic methods and radicals present are followed.

An intermediate aldehyde of formula III may be prepared as outlined in Scheme I and described in Example 1, parts f.-1. for a compound in which Q is 3,4-dichlorophenyl, $Q^1$ is hydrogen and $Q^2$ is phenyl. Alkylation of the anion of 3,4-dichlorophenylacetonitrile with 1-bromo-2-(2-tetrahydropyranyloxy)ethane (conveniently prepared from 2-bromoethanol and dihydropyran using a strong acid exchange resin as catalyst) gives a nitrile of formula VI. Reduction of the nitrile gives a corresponding amine of formula VII which can be acylated using benzoic anhydride in the presence of a suitable base to give an amide of formula VIII. Alkylation of the amide with methyl iodide followed by hydrolysis of the acetal gives an alcohol of formula IX, which can be oxidized to give an intermediate of formula III. Alternatively, the alcohol of formula IX may be converted into an alkylating agent of formula IV using a conventional procedure.

An intermediate of formula III or of formula IV wherein the center marked with * has the (S) absolute configuration can be prepared from a corresponding compound of formula IX which may be obtained from a racemic compound of formula VII as outlined in Scheme II and described in Example 13, parts a.-f. for a compound in which Q is 3,4-dichlorophenyl, $Q^1$ is hydrogen and $Q^2$ is phenyl. Hydrolysis of an acetal of formula VII gives an amine of formula X. Salt formation with D-tartaric acid followed by crystallization, recrystallization and treatment with aqueous base gives the (S)-enantiomer of the compound of formula X. Treatment with ethyl chloroformate followed by reduction of the resulting carbamate gives the (S)-enantiomer of the amine of formula XI. Treatment of the amine with benzoyl chloride gives the (S)-enantiomer of the compound of formula IX, which can be oxidized to give the (S)-enantiomer of the compound of formula III or converted into the (S)-enantiomer of the compound of formula IV.

An intermediate amide of formula V may be prepared by alkylating a corresponding piperidine of formula IIa using a similar method to that described in (a) above or by any other conventional method.

The utility of a compound of the invention or a pharmaceutically acceptable salt thereof (hereinafter, collectively referred to as a "Compound") may be demonstrated by standard tests and clinical studies, including those disclosed in the EPA publications noted above, such as EPA 428434 or EPA 474561 (or U.S. Pat. No. 5,236,921), and those described below.

Neurokinin A (NKA) Receptor-binding Assay (Test A)

The ability of a Compound of the invention to antagonize the binding of NKA at the NK2 receptor may be demonstrated using an assay using the human NK2 receptor expressed in Mouse Erythroleukemia (MEL) cells by using EL cell membranes (MELM) which bear high-affinity and selective NK2 receptors and which is carried out as follows.

Figure 1:
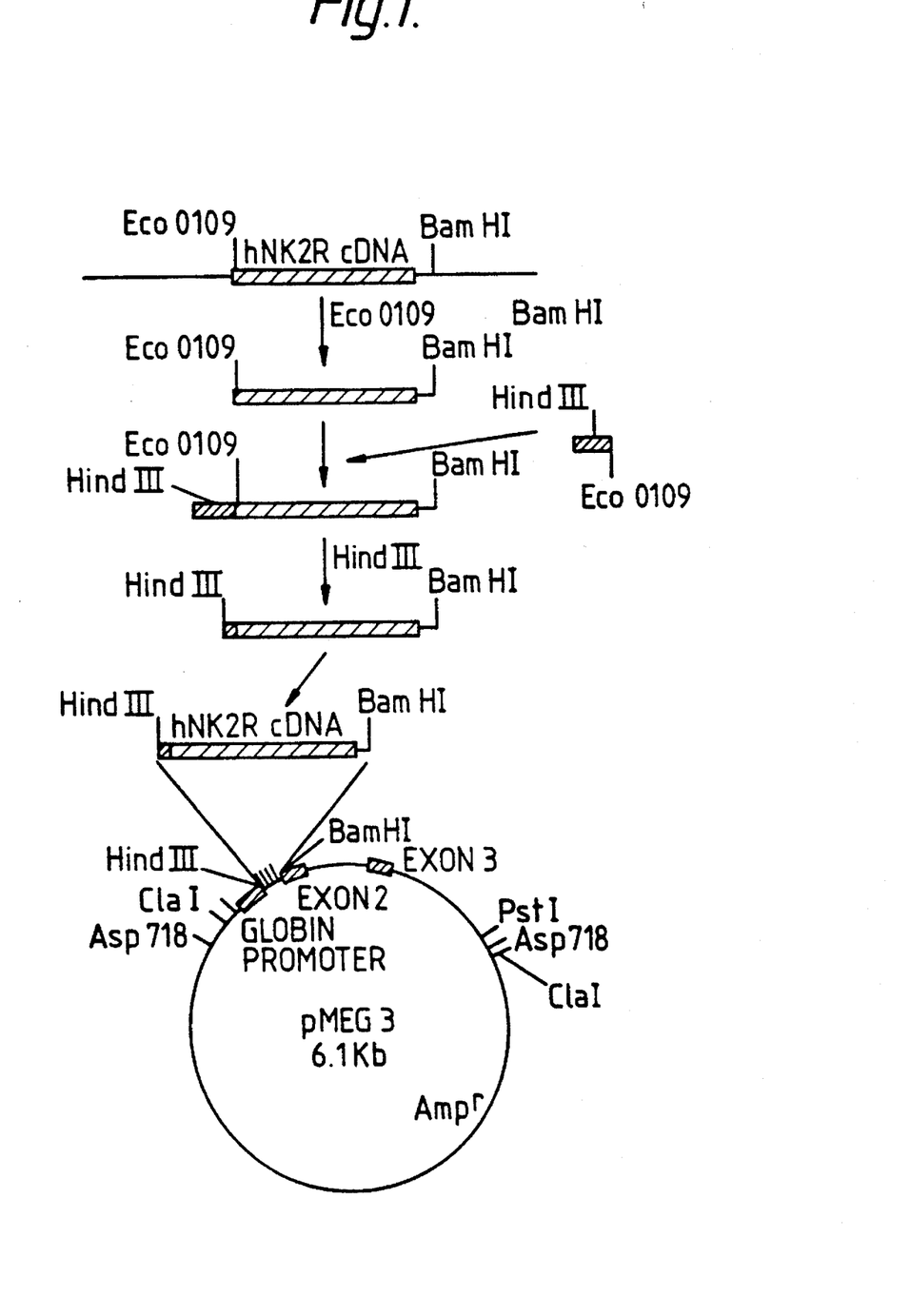
FIG. 1 shows construction of the MEL cell expression vector construct pMEG3/hNK2R.
Figure 2:
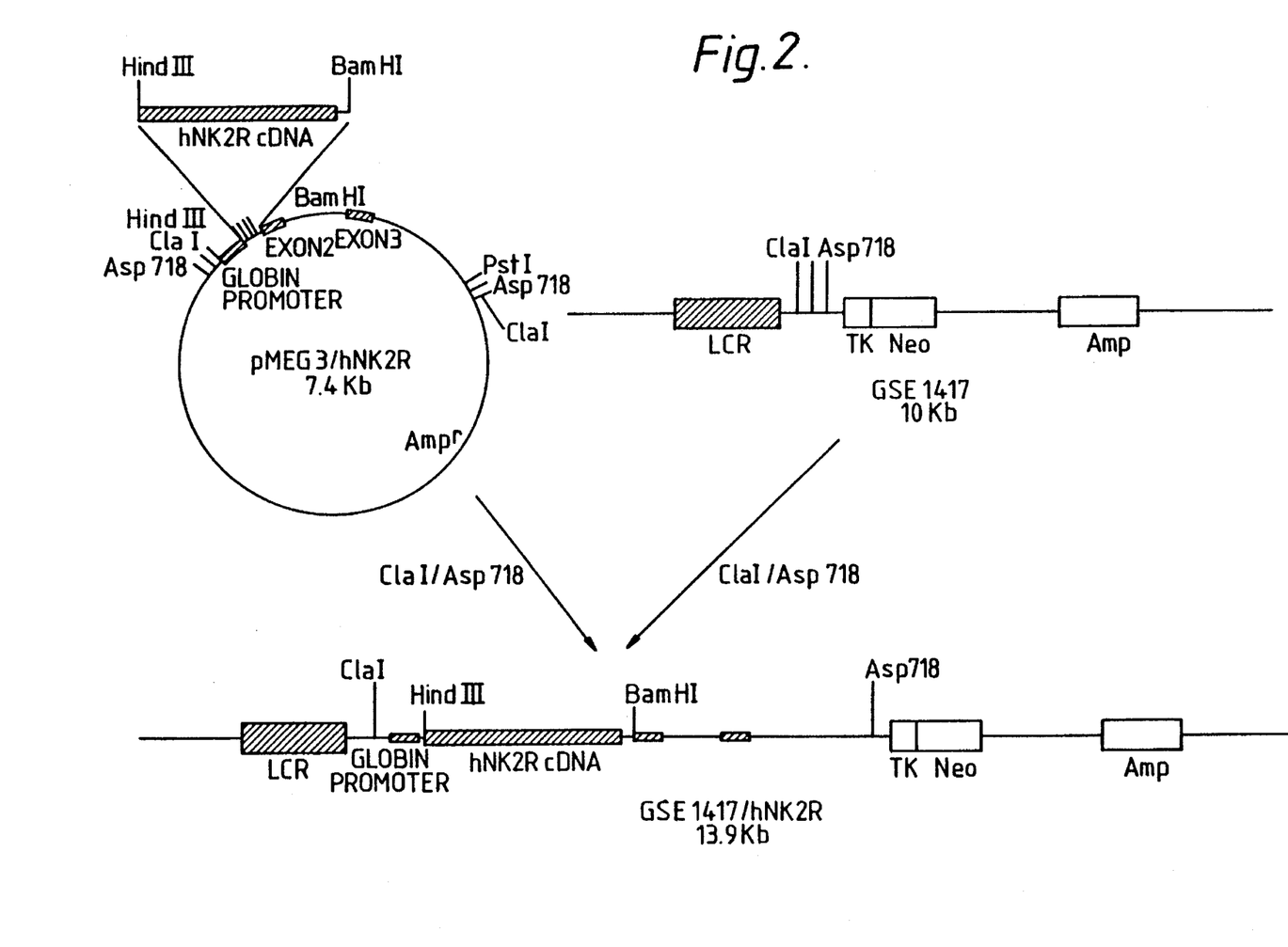
FIG. 2 shows construction of the expression vector construct GSE1417/hNK2R.
Figure 3:
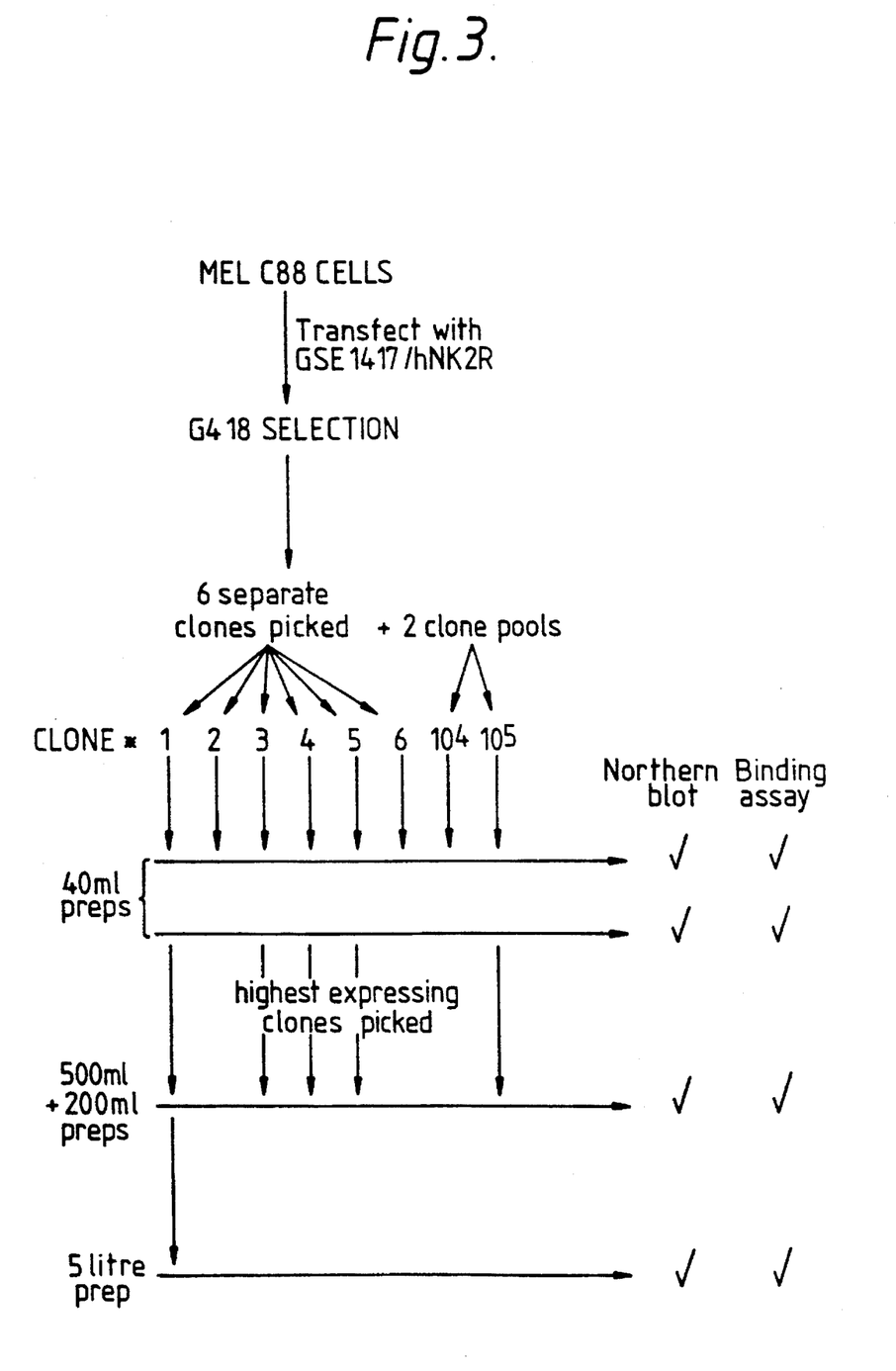
FIG. 3 shows expression of human NK2 receptor in MEL C88 cells.

MEL Cell Expression of Human NK2 Receptor (hNK2R):

Heterologous protein expression in Mouse Erythroleukemia (MEL) cells uses the human globin locus control region (LCR) (F. Grosveld et al., *Cell* (1987) 51, 975–985). The cDNAs are inserted between the human beta-globin promoter and the second intron of the human beta-globin gene, and this expression cassette is then placed downstream of the LCR and transfected into MEL cells (M. Needham et al., *Nucl. Acids Res.* (1992) 20, 997–1003). Human NK2 receptor cDNA (A. Graham et al., *Biochem. Biophys. Res. Commun.* (1991) 177, 8–16) was isolated from human lung RNA by polymerase chain reaction and DNA sequenced. Human NK2 receptor cDNA was subcloned into a shuttle vector (pMEG3) containing the beta-globin promoter and the 3' portion of the human beta-globin gene (FIG. 1). Human NK2 receptor cDNA was restricted with Eco 0109 (5' end) and Bam HI (3' end). An oligonucleotide linker-adaptor containing an internal Hind III site and a 3' end Eco 0109 site was ligated to the hNK2R cDNA fragment. The sequence of the top strand oligonucleotide =5'd(GCGCAAGCTTATGGG) (SEQ ID NO:1) and the bottom strand oligonucleotide =5'd(GTCCCCATAAGCTTGCGC) (SEQ ID NO:2). These were annealed and ligated to the hNK2R fragment by standard methods. Following cleavage with Hind III, the resulting fragment was cloned into the Hind III and Bam HI sites in the polylinker of the shuttle vector pMEG3. The construct (pMEG3/hNK2R) was verified by restriction mapping and sequencing the 5' end and 3' end junctions of cDNA/vector. This was then transformed into *E.coli* DH5 alpha, and plasmid DNA was isolated by standard methods and verified by restriction mapping and DNA sequencing. A ClaI/Asp718 cassette carrying the beta-globin promoter, human NK2 receptor cDNA and the 3' beta-globin gene fragment was excised and subcloned downstream of the LCR in plasmid pGSE1417 (FIG. 2). The pMEG3/hKNK-2R construct was cleaved with ClaI and Asp718 and cloned directly into the ClaI and Asp718 sites (3' of LCR) in the expression vector GSE1417. The construct GSE1417/hNK2R (13.9kb) was verified by restriction mapping. *E.coli* DH5 alpha was transformed and recombinant plasmids verified by restriction mapping. MEL C88 cells (A. Deisseroth et al., *Cell* (1978) 15, 55–63) were electroporated (M. Antoniou, *Methods Molecular Biology* (1991) 7, 421–434) with PvuI linearized pGSE1417/human NK2 receptor DNA. Directly after transfection, cells were diluted in culture medium to $10^4$ and $10^5$ cell per mL and 1 mL aliquots transferred to each well of a 24-well plate. G418 was added to a concentration of 1 mg/mL 24 hours after the transfection to select for stable transfectants. Individual clones were picked or pooled to generate populations seven to ten days after the addition of selective medium. FIG. 3 shows the strategy used to isolate transfected MEL/human NK2 receptor cell line. For expression studies, cells were maintained in exponential growth for a period of four days, and then dimethyl sulfoxide (DMSO) was added to a final concentration of 2% (v/v) to induce differentiation and hence expression. Samples were taken 4 days post induction for mRNA and NKA binding analyses. The results indicated that clone #1 expresses hNK2R at the highest level (both hNK2R mRNA and specific NKA binding). This clone was scaled up and is now routinely fermented at 20 liter scale per month and supplied for use in Test A.

Membrane preparations (MELM) prepared from the MEL cells containing high-affinity NK2 receptors were prepared according to a published protocol (D. Aharony, et al., *Neuropeptides* (1992) 23, 121–130) with the following minor modifications: (1) Iodoacetamide (1 mM) was included in the homogenization buffer; (2) Homogenization was as published but for a shorter period of 10 seconds once and at a slower speed (setting 10); and (3) The equilibration step with KCl/EDTA was not performed. In a typical preparation, binding of $^3$H-NKA (2.5 nM) to MELM was highly specific (88±4%) and linearly dependent on the protein concentration, with significant binding detected as low as 26 μg protein/mL. Equilibrium-competion experiments demonstated binding to high-affinity, high-density receptors with $K_D$=1187 nM, $B_{max}$=2229 fmol/mg protein.

The radio ligand $^3$H-neurokinin A ($^3$H-NKA) as [4,5-$^3$H-Leu$^9$]-NKA (typical specific activity, 117 Ci/mmol) is obtained by custom synthesis from Cambridge Research Biochemicals and is >95% pure. Repeated HPLC analysis demonstrated that the ligand is stable under proper storage conditions (silanized vials with 0.2% mercaptoethanol, under argon). Also, no degradation or metabolism is apparent in the receptor-binding assay.

The assay is carried out using an incubation buffer consisting of 50 mM Tris HCl (pH 7.4), 5 mM Mg$^{++}$, 100 μM thiorphan 1 nM $^3$H-NKA, 0.02% (w:v) BSA, 30 mM K$^+$, and 300 μM dithiothreitol; and the concentration of membrane protein is held at approximately 0.05–0.025 mg per tube. Nonspecific binding is routinely defined with 1 μM NKA. Each tube receives the following: 150 μL incubation buffer, 20 μL $^3$H-NKA, 20 μL Compound, NKA or buffer as appropriate, and 125 μL membrane suspension. The reaction is initiated by the addition of the membranes. The tubes are incubated for 60 min at 25° C. in a shaking water bath. The reaction is terminated by washing the tubes with 10 mL of ice-cold 50 mM Tris HCl using a Brandel cell harvesting system using Whatman GF/B filters which have been soaked at least 4 hours at room temperature in 0.01% (w:v) polyethylenimine to collect the membranes. The filters are deposited in scintillation vials and read in a Beckman LS 6000LL Scintillation Counter. The binding constant $K_i$ is calculated by standard methods and is typically the mean of several such determinations. The $K_i$ values may be converted to negative logarithms and expressed as –log molar $K_i$ (i.e. p$K_i$).

In an initial use of this assay, the IC$_{50}$ measured for the standard compound L-659,877 was found to be 30 nM versus $^3$H-NKA binding to MELM. The selectivity of a Compound for binding at the NK2 receptor may be shown by determining its binding at other receptors using standard assays, for example, one using a tritiated derivative of SP in a tissue preparation selective for NK1 receptors or one using a tritiated derivative of NKB in a tissue preparation selective for NK3 receptors.

Guinea Pig Trachea Assay (Test B)

In the test described below either NKA or [β-ala$^8$]-NKA(4–10) is used as an agonist. The chosen agonist is referred to as AG throughout the description. The ability of a Compound of the invention to antagonize the action of AG in a pulmonary tissue may be demonstrated using a functional assay in guinea pig trachea, which is carried out as follows.

Male guinea pigs are killed by a sharp blow to the back of the head. The trachea are removed, trimmed of excess tissue and divided into two segments. Each segment is suspended as a ring between stainless steel stirrups in water-jacketed (37.5° C.) tissue baths containing a physiological salt solution of the following composition (mM): NaCl, 119; KCl 4.6; CaCl$_2$, 1.8; MgCl$_{2, 0.5}$; NaH$_2$PO$_4$, 1; NaHCO$_3$, 25; glucose, 11; thiorphan, 0.001; and indometha-cin, 0.005; gassed continuously with 95% O$_2$–%5 CO$_2$. Initial tension placed on each tissue is 1 g, which is maintained throughout a 0.5 to 1.5 hour equilibration period before addition of other drugs. Contractile responses are measured on a Grass polygraph via Grass FT-03 force transducers.

Tissues are challenged repetitively with a single concentration of AG (10 nM) with intervening 30 min periods with washing to allow the tension to return to baseline levels. The magnitude of the contractions to AG reaches a constant level after two challenges, and each Compound is tested for inhibition of responses to AG by addition to the tissue bath 15 minute before the third or subsequent exposure to the agonist. The contractile response to AG in the presence of Compound is compared to that obtained with the second AG challenge (in the absence of Compound). Percent inhibition is determined when a Compound produces a statistically significant ($p<0.05$) reduction of the contraction and is calculated using the second contractile response as 100%.

Potencies of selected Compounds are evaluated by calculating apparent dissociation constants ($K_B$) for each concentration tested using the standard equation:

$$K_B=[antagonist]/(dose\ ratio-1)$$

where dose ratio=antilog[(AG –log molar EC$_{50}$ without Compound)—(AG –log molar EC$_{50}$ with Compound)]. The $K_B$ values may be converted to the negative logarithms and expressed as –log molar $K_B$ (i.e. p$K_B$). For this evaluation, complete concentration-response curves for AG are obtained in the absence and presence of Compound (30 min incubation period) using paired tracheal rings. The potency of AG is determined at 50% of its own maximum response level in each curve. The EC$_{50}$ values are converted to the negative logarithms and expressed as –log molar EC$_{50}$. Maximum contractile responses to AG are determined by expressing the maximum response to AG as a percentage of the contraction caused by carbachol (30μM), added after the initial equilibration period. When a statistically significant ($p<0.05$) reduction of the maximum response to AG is produced by a compound, the percent inhibition is calculated relative to the percentage of carbachol contraction in the untreated, paired tissue used as 100%.

Guinea Pig Labored Abdominal Breathing (Dyspnea) Assay (Test C)

Activity of a Compound of the invention as an antagonist of NKA at the NK2 receptor also may be demonstrated in vivo in laboratory animals, for example by adapting a routine guinea pig aerosol test described for evaluation of leukotriene antagonists by Snyder, et al. (Snyder, D. W., Liberati, N.J. and McCarthy, M. M., Conscious guinea-pig aerosol model for evaluation of peptide leukotriene antagonists. *J. Pharmacol. Meth.* (1988) 19, 219). Using the clear plastic chamber described previously by Snyder et al. to secure guinea pigs for a head-only aerosol exposure to bronchoconstrictor agonists, agonist is administered by aerosol to six conscious guinea pigs simultaneously during each maneuver. The tachykinin NK2-selective agonist, [β-ala$^8$]-NKA(4–10), 3×10$^{-5}$ M, is aerosolized from a Devilbiss Model 25 ultrasonic nebulizer into an air stream entering the chamber at a rate of 2 L/minute.

Guinea pigs (275–400 g) are fasted for approximately 16 hours prior to experimentation. Compounds to be evaluated for blockade of effects of [β-ala$^8$]-NKA(4–10) or their vehicle (10% PEG400 in saline) are administered p.o. or i.v. at various times before aerosol agonist challenge. All animals are pretreated with atropine (10 mg/kg, j.p., 45 minutes pretreatment) indomethacin (10 mg/kg, i.p., 30 minutes pretreatment), propranolol (5 mg/kg, i.p., 30 minutes pretreatment), and thiorphan (1 mg/ml aerosol for 5 minutes, 15 minutes pretreatment)

Aerosol challenge with the agonist produces an initial increase in respiratory rate followed by a decrease with early signs of minor involvement of the abdominal muscles. The respiratory rate. decreases further and the breathing becomes more labored with greater involvement of the abdominal muscles as exposure continues. The distinctly recognizable end point is the point where the breathing pattern of the guinea pig is consistently slow, deep, and deliberate, showing marked involvement of the abdominal muscles. Time, in seconds, from the onset of aerosol challenge to this end point is determined for each animal by using a stopwatch. The animals generally collapse after reaching the end point and donor recover from the agonist-induced respiratory distress. Antagonists result in an increase in the time to reach the end point. Animals receive the aerosol administration of agonist for a maximum time of 780 seconds.

Differences between drug treated groups and corresponding vehicle treated control groups are compared using Student's t-test for unpaired observations.

Clinical studies to demonstrate the efficacy of a Compound of the invention may be carried out using standard methods. For example, the ability of a Compound to prevent or treat the symptoms of asthma or asthma-like conditions may be demonstrated using a challenge of inhaled cold air or allergen and evaluation by standard pulmonary measurements such as, for example, $FEV_1$ (forced expiratory volume in one second) and FVC (forced vital capacity), analyzed by standard methods of statistical analysis.

It will be appreciated that the implications of a Compound's activity in Test A or Test B is not limited to asthma, but rather, that the test provides evidence of general antagonism of NKA. In general, the Compounds of the invention which were tested demonstrated statistically significant activity in Test A with a $K_i$ of 1 μM or much less. For example, the compound described in Example 10 was typically found to have a $K_i$ of 40 nM, and that of Example 16 a $K_i$ of 1.5 nM. In Test B, a $pK_B$ of 5 or greater was typically measured for a Compound of the invention. For example, a $pK_B$ of 7.8 was measured for the compound described in Example 10, and a $pK_B$ of 8.4 was measured for the compound described in Example 16. It should be noted that there may not always be a direct correlation between the activities of Compounds measured as $K_i$ values in Test A and the values measured in other assays, such as the $pK_B$ measured in Test B. No untoward side-effect following i.v. or p.o. dosing of a Compound of the invention in Test C has been noted. In Test C following oral administration at 5 82 mol/kg two hours prior to challenge with the agonist, the compound of Example 16 for example exhibited 100% protection, fully protecting all five of the animals tested.

As discussed above, a compound of formula I or a pharmaceutically acceptable salt thereof possesses NKA antagonist properties. Accordingly, it antagonizes at least one of the actions of NKA which are known to include bronchoconstriction, increased microvascular permeability, vasodilation and activation of mast cells. Accordingly, one feature of the invention is the use of a compound of formula I or a pharmaceutically acceptable salt thereof in the treatment of a disease in a human or other mammal in need thereof in which NKA is implicated and antagonism of its action is desired, such as, for example, the treatment of asthma or a related disorder. In addition, another feature of the invention is provided by the use of a compound of formula I or a salt thereof as a pharmacological standard for the development and standardization of new disease models or assays for use in developing new therapeutic agents for treating the diseases in which NKA is implicated or for assays for their diagnosis.

When used in the treatment of such a disease, a compound of the invention is generally administered as an appropriate pharmaceutical composition which comprises a compound of formula I or a pharmaceutically acceptable salt thereof as defined hereinbefore and a pharmaceutically acceptable diluent or carrier, the composition being adapted for the particular route of administration chosen. Such a composition is provided as a further feature of the invention. It may be obtained employing conventional procedures and excipients and binders, and it may be one of a variety of dosage forms. Such forms include, for example, tablets, capsules, solutions or suspensions for oral administration; suppositories for rectal administration; sterile solutions or suspensions for administration by intravenous or intramuscular infusion or injection; aerosols or nebulizer solutions or suspensions for administration by inhalation; or powders together with pharmaceutically acceptable solid diluents such as lactose for administration by insufflation.

For oral administration a tablet or capsule containing up to 250 mg (and typically 5 to 100 mg) of a compound of formula I may conveniently be used. For administration by inhalation, a compound of formula I will be administered to humans in a daily dose range of, for example, 5 to 100 mg, in a single dose or divided into two to four daily doses. Similarly, for intravenous or intramuscular injection or infusion a sterile solution or suspension containing up to 10% w/w (and typically 0.05 to 5% w/w) of a compound of formula I may conveniently be used.

The dose of a compound of formula I to be administered will necessarily be varied according to principles well known in the art taking account of the route of administration and the severity of the condition and the size and age of the patient under treatment. However, in general, the compound of formula I will be administered to a warm-blooded animal (such as man) so that a dose in the range of, for example, 0.01 to 25mg/kg (and usually 0.1 to 5 mg/kg) is received. It will be understood that generally equivalent amounts of a pharmaceutically acceptable salt of a compound of formula I may be used.

The invention will now be illustrated by the following non-limiting examples in which, unless stated otherwise:

(i) temperatures are given in degrees Celsius (° C.); operations were carried out at room or ambient temperature, that is, at a temperature in the range of 18°–25° C.;

(ii) organic solutions were dried over anhydrous magnesium sulfate; evaporation of solvent was carried out using a rotary evaporator under reduced pressure (600–4000 pascals; 4.5–30 mm Hg) with a bath temperature of up to 60° C.;

(iii) chromatography means flash chromatography on silica gel; reversed phase chromatography means chromatography over octadecylsilane (ODS) coated support having a particle diameter of 32–74 μ, known as "PREP-40-ODS" (Art 731740-100 from Bodman Chemicals, Aston, Pa., USA); thin layer chromatography (TLC) was carried out on silica gel plates;

(iv) in general, the course of reactions was followed by TLC and reaction times are given for illustration only;

(v) melting points are uncorrected and (dec) indicates decomposition; the melting points given are those obtained for the materials prepared as described; polymorphism may result in isolation of materials with different melting points in some preparations;

(vi) final products had satisfactory proton nuclear magnetic resonance (NMR) spectra;

(vii) yields are given for illustration only and are not necessarily those which may be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 300 MHz using perdeuterio dimethyl sulfoxide (DMSO-$d_6$) as solvent; conventional abbreviations for signal shape are used; for AB spectra the directly observed shifts are reported; when given, coupling constants (J) are in Hz; Ar designates an aromatic proton when such an assignment is made;

(ix) chemical symbols have their usual meanings; SI units and symbols are used;

(x) reduced pressures are given as absolute pressures in pascals (Pa); elevated pressures are given as gauge pressures in bars;

(xi) solvent ratios are given in volume:volume (v/v) terms; and (xii) mass spectra (MS) were run with an electron energy of 70 electron volts in the electron impact (EI) mode using a direct exposure probe; where indicated ionization was effected by chemical ionization (CI) or fast atom bombardment (FAB); values for m/z=are given; generally, only ions which indicate the parent mass are reported.

Example 1. N-[2-(3,4-Dichlorophenyl)-4-[4-(1-hydroxyethyl)piperidino] butyl]-N-methylbenzamide hydrochloride.

A solution of 4-(1-hydroxyethyl)piperidine (450 mg) and N-[2-(3,4-dichlorophenyl)-3-formylpropyl]-[-methylbenzamide (1.18 g) in methanol (25 mL) was adjusted to pH 5.5 by addition of glacial acetic acid. This mixture was cooled to 0° C. and treated with sodium cyanoborohydride (304 mg). The resulting mixture was allowed to warm to room temperature and was stirred for 72 hours. The solvent was evaporated and the residue was dissolved in dichloromethane (100 mL) and washed successively with 1N aqueous sodium hydroxide, water (2×) and brine. The organic extract was dried, filtered and evaporated. Purification by chromatography (93:7:0.1 chloroform/methanol/aqueous ammonium hydroxide) afforded the pure title compound as a white foam (775 mg, 48%). Treatment of a solution of this foam (238 mg) in diethyl ether (5 mL) with hydrogen chloride (g) afforded the hydrochloride salt of the title compound (208 mg) as a white solid; mp 94°–98° C.; NMR: 7.60–7.34 (m,5), 7.21–6.98 (m,3), 3.87–3.72 (m,2), 3.55 (br s,3), 3.28 (re, 1), 3.15–2.77 (m,4), 3.07,2.76 (2s, NCH$_3$), 2.17–1.80 (br m,3), 1.54 (br m, 4), 1.17 (d,3, J=6.2). MS (CI): m/z=465((M+1), 37Cl), 463((M+1), $^{35}$Cl). Analysis for $C_{25}H_{32}Cl_2N_2O_2$.1.0 HCl .0.50 $H_2O$: Calculated: C, 59.01; H, 6.73; N, 5.50; Found: C, 58.98; H, 6.63; N, 5.44.

The starting material 4-(1-hydroxyethyl)piperidine was prepared as follows.

a. 1-(Benzyloxycarbonyl)-4-piperidine carboxylic acid. A solution of isonipecotic acid (5.0 g) in 10% aqueous sodium carbonate (100 mL) was cooled to 0° C. and treated with benzyl chloroformate (7.93 g). The resulting biphasic mixture was allowed to warm to room temperature over 2 hours, at which time it became homogeneous. The mixture was washed with ether (2×), was acidified to approximately pH 2 by addition of concentrated hydrochloric acid. The aqueous solution was extracted with ether (2×). The organic extracts were washed with brine, combined, dried, filtered and evaporated to leave a clear oil which slowly crystallized on standing (9.64 g); NMR (CDCl$_3$): 7.36 (m,5, $C_6H_5$), 5.13 (s,2, PhCH$_2$), 4.10 (br d,2, J=12.6 eq-H-C(2)), 2.96 (brdd, 2, j=11.2, 12.6, ax-H-C(2)), 2.52 (re, 1, H-C(4)), 1.93 (br d,2, J=10.8, eq-H-C(3) ), 1.70 (m,2, ax-H-C(3) ); MS (CI): m/z=264(M+1).

b. H-Methoxy-H-methyl-l-(Benzyloxycarbonyl)piperidine-4-carboxamide. A solution of 1-(benzyloxycarbonyl)-4-piperidinecarboxylic acid (2.0 g), N,O-dimethylhydroxylamine hydrochloride (890 mg), 1-(3-dimethylaminopropyl)-3-ethylcarbodiimide hydrochloride (1.75 g), 4-dimethylaminopyridine (93 mg) and triethylamine (2.31 g) in dichloromethane (50 mL) was stirred at room temperature for 22 hours. The mixture was poured into 2N hydrochloric acid (50 mL) and extracted with ethyl acetate (3×). The organic extracts were washed sequentially with 2N hydrochloric acid, 10% aqueous sodium bicarbonate and brine, combined, dried, filtered and evaporated to afford the amide as a clear syrup (1.97 g); NMR (CDCl$_3$): d 7.35 (m,5, $C_6H_5$), 5.13 (s,2, PhCH$_2$), 4.25 (br,2), 3.71 (s,3, OCH$_3$), 3.19 (s,3, NCH$_3$), 2.86 (br,3), 1.71 (br,4).

c. 4-Acetyl-l-(benzyloxycarbonyl)piperidine. A solution of methyllithium (7 mL of a 1.4 M solution in diethyl ether) in tetrahydrofuran (15 mL) was cooled to -60° C. and treated dropwise with a solution of N-methoxy-N-methyl-1-(benzyloxycarbonyl)piperidine-4-carboxamide (2.50 g) in tetrahydrofuran (10 mL). The resulting solution was stirred at –60° C. for 2 hours, was warmed to 0° C. and quenched with 1N hydrochloric acid (10 mL). The mixture was diluted with 1N hydrochloric acid and extracted with ethyl acetate. The organic.extract was washed sequentially with 1N hydrochloric acid and brine, dried, filtered and evaporated to afford a pale yellow syrup. Purification by chromatography (dichloromethane) afforded the ketone as a white solid (1.12 g); NMR: 7.35 (m, 5, $C_6H_5$), 5.06 (s,2, PhCH$_2$), 3.96 (m, 2), 2.86 (m,2), 2.53 (m, 1), 2.11 (s,3), 1.81 (m, 2), 1.30 (m, 2).

d. (RS)-1-Benzyloxycarbonyl-4-(1-hydroxyethyl)piperdine. A solution of 4-acetyl-1-(benzyloxycarbonyl)piperidine (980 mg) in methanol (25 mL) was treated with sodium borohydride (142 mg), added portionwise over 10 minutes. The resulting reaction mixture was stirred for 3 hours and evaporated. The residue was dissolved in dichloromethane (50 mL) and washed sequentially with water (2×) and brine. The organic extract was dried, filtered and evaporated to afford the alcohol as a clear syrup (959 mg); NMR: 7.35 (m, 5, $C_6H_5$), 5.06 (s,2, PhCH$_2$), 4.03 (m,2), 3.54 (m, 1), 2.70 (br m, 2), 1.82 (m, 1), 1.64 (m, 1), 1.38 (m, 1), 1.12 (m,2), 1.01 (d,3, J=6.3).

e. 4-(1-Hydroxyethyl)piperidine. A solution of 1-benzyloxycarbonyl-4-(1-hydroxyethyl)piperidine (959 mg) in ethanol (40 mL) was hydrogenated over 10% palladium on carbon (100 mg) at a hydrogen pressure of 3.45 bar for 16 hours. The resulting mixture was filtered through diatomaceous earth and evaporated to afford the piperdine as a clear oil (450 mg); NMOS: 3.33 (m, 1), 3.02 (br d,2, J=11.9), 2.46 (m,2), 1.73 (br d,1, J=12.7), 1.51 (br d,1, J=12.1), 1.26–1.03 (m,3), 1.00 (d,3, J=6.3).

The starting material N-[2-(3,4-dichlorophenyl)-3-formylpropyl] -N-methylbenzamide was prepared as follows.

f. 1-Bromo-2-(2-tetrahydropyranyloxy)ethane. To a mechanically stirred solution of dihydropyran (1000 mL) and Amberlyst 15 (10.0 g) in hexane (2000 mL) was added bromoethanol (985 g) dropwise over a period of 1.5 hours in a cold water bath to maintain an internal temperature of 35°–40° C. After being stirred overnight at room temperature, the reaction mixture was passed through a silica gel column (3×18 inches), and eluted with hexane (6 L). The eluate was evaporated to give an amber liquid which was distilled through a 2 inch vigreau collecting the material boiling between 75°–95° C. at 3,300–4,700 Pa (25–35 mm Hg). This material was redistilled to give the ether (1195.5 g, 80°–90° C. at 20 mm Hg) as an oil; NMR: 4.68 (m, 1), 4.01 (m, 1), 3.89 (m, 1), 3.77 (m, 1), 3.52 (m,3), 1.75–1.50 (m, 6).

g. α-[2-(2-Tetrahydropyranyloxy)ethyl]-3,4-dichlorophenylacetonitrile. To a solution of sodium hydride (218.0 g of a 55% oil suspension) in tetrahydrofuran (4 L) at 10° C. in an ice/water bath was added 3,4-dichlorophenylacetonitrile (893.0 g) in tetrahydrofuran (2 L) over a period of 45 minutes, and the resulting solution was allowed to stir for 2 hours at room temperature. The mixture was cooled in an ice/water bath and 1-bromo-2-(2-tetrahydropyranyloxy)ethane (1076.0 g) was dropped in as a neat oil over a period of 25 minutes. The mixture was stirred overnight at room temperature and divided into four 2-liter portions. Each portion was diluted with saturated ammonium chloride (3 L) and extracted with ether (500 mL). The combined organic layers were washed (aqueous ammonium chloride), dried, and evaporated. The resulting material was chromatographed, with hexane/dichloromethane (gradient 100:0, 0:100) as eluent, to give the nitrile (932 g) as an oil; NMR: 7.47 (m,4), 7.20 (m,2), 4.57 (m,2), 4.08 (m, 2), 3.85 (m, 4), 3.54 (m,3), 3.37 (m, 1), 2.15 (m, 4), 1.77 (m, 4), 1.56 (m,8).

h. 2-(3,4-Dichlorophenyl)-4-(2-tetrahydropyranyloxy)butylamine. To a solution of the above nitrile (128.3 g) in 95% ethanol (1.1 L) and concentrated ammonium hydroxide (550 mL) was added Raney Nickel (25.0 g). The mixture was hydrogenated under a hydrogen atmosphere at room temperature and 53 psi for 1.5 days. The mixture was filtered through diatomaceous earth to remove the catalyst, and the resulting filtrate was evaporated. The resulting material was chromatographed, with dichloromethane:methanol (gradient 100:0, 95:5) as eluent, to give the amine (91 g) as an oil; NMR: 7.40 (s,1), 7.38 (s,1), 7.32 (d,1, J=2.1), 7.28 (d, 1, J=2.0), 7.07 (dd,1, J=2.1, 4.9), 7.04! .(dd, 1, J=2.1, 4.9 ), 4.50 (m, 1 ), 4.43 (m, 1 ), 3.70 (m, 4 ), 3.45 (m, Z), 3.27 (re, 1), 3.17 (re, 1), 2.97–2.75 (m, 6), 2.00 (m,2), 1.82–1.66 (m, 6), 1.53 (m,8), 1.18 (bs,4); MS (CI): m/z=318(M+1).

i. N-[2-(3,4-Dichlorophenyl)-4-(2-tetrahydropyranyloxy)butyl]benzamide. To a solution of the above amine (2.5 g) in dichloromethane (35 mL) was added triethylamine (1.1 mL) and benzoic anhydride (1.85 g), and the resulting solution was allowed to stir for 45 minutes. The mixture was washed (0.2 N hydrochloric acid, 1 N sodium hydroxide, water), dried, and evaporated to give the amide (3.3 g) as an oil; NMR: 7.63 (m, 4), 7.46 (m,2), 7.37 (m, 8), 7.09 (m,2), 6.22 (m,2), 4.50 (m, 1), 4.43 (re, 1), 3.8 (m, 5), 3.63 (m, 1), 3.5 (m, 4), 3.36 (m, 1), 3.23 (m, 1), 3.11 (m,2), 2.06 (m,2), 1.90–1.77 (m, 4), 1.68 (m, 2), 1.51 (m, 8); MS (CI): m/z=338[(M+1)-tetrahydropyranyl].

j. H-[2-(3,4-Dichlorophenyl)-4-(2-tetrahydropyranyloxy)butyl]-N-methylbenzamide. To a solution of the above amide (3.3 g) in dimethyl sulfoxide (20 mL) was added powdered potassium hydroxide (1.6 g), followed by iodomethane (1.0 mL) after 15 minutes. After 1 hour, the mixture was diluted with water (330 mL) and extracted with dichloromethane (2×50 mL). The combined organic extracts were dried and evaporated to give the H-methylamide (3.1 g) as an oil; MS (CI): m/z=352[(M+1)-tetrahydropyranyl].

k. N-[2-(3,4-Dichlorophenyl)-4-hydroxybutyl]-N-methylbenzamide. To a solution of the above amide (10.5 g) in tetrahydrofuran (100 mL) was added 6 N hydrochloric acid (50 mL), and the resulting solution was allowed to stir overnight. The mixture was neutralized with 10 N sodium hydroxide, diluted with water (200 mL), and extracted with dichloromethane. The organic layer was dried and evaporated. The resulting yellow solid was suspended in ether and filtered to give the alcohol (8.4 g) as a white solid; MS (CI): m/z=352(M+1).

l. N-[2-(3,4-Dichlorophenyl)-3-formylpropyl]-N-methylbenzamide. A solution of oxalyl chloride (878 mg) in dichloromethane (5 mL) was cooled to −78° C. and was treated dropwise with a solution of dimethyl sulfoxide (595 mg) in dichloromethane (2 mL). The resulting mixture was stirred at −78° C. for 15 minutes, and was treated dropwise with a solution of N-[2-(3,4-dichlorophenyl)-4-hydroxybutyl]-H-methylbenzamide (1.22 g) in dichloromethane (10 mL)/dimethyl sulfoxide (2 mL). The mixture was stirred at −78° C. for 1 hour, was treated with triethylamine (1.75 g), warmed to room temperature and stirred for 1 hour. The mixture was poured into water and extracted with dichloromethane. The organic extract was washed sequentially with water (2×) and brine, dried, filtered through Florisil and evaporated to afford the aldehyde as a pale yellow oil (1.18 g); MS (CI): m/z= 352((M+I), $^{37}$Cl), 350((M+1) $^{35}$Cl)

Example 2. N-[2-(3,4-Dichlorophenyl)-4-[4-(1-hydroxybutyl)piperidino]butyl]-N-methylbenzamide hydrochloride.

Using a procedure similar to that described in Example 1, except using 4-(1-hydroxybutyl)piperidine, prepared by a similar sequence as described in Example 1(b–e), except using propylmagnesium chloride in place of methyllithium (step b), and the aldehyde prepared as described in Example 1.1., the hydrochloride of the title compound was obtained as a white powder, mp 92°–95° C.; NMR: 7.60–7.36 (m, 5), 7.20–6.97 (m,3), 3.82–3.76 (m, 2), 3.58–3.47 (m, 2), 3.36 (re, 1), 3.25 (br s,1), 3.20–2.80 (m,4), 3.07, 2.75 (2s, NCH$_3$), 2.17–1.84 (br m, 4), 1.67–1.30 (m,7), 0.94 (br s,3); MS (CI): m/z=493((M+i), $^{37}$Cl), 491((M+1), $^{35}$Cl). Analysis for $C_{27}H_{36}Cl_2N_2O_2 \cdot 1.0$ HCl·1.0 H$_2$O: Calculated: C, 59.40; H, 7.20; N, 5.13; Found: C, 60.43; H, 7.05; N, 5.00.

Example 3. N-[2-(3,4-Dichlorophenyl)-4-(4-propionylpiperidino) butyl]-N-methylbenzamide hydrochloride.

A solution of ethylmagnesium chloride (0.47 mL of a 2M solution in tetrahydrofuran) in tetrahydrofuran (2 mL) was cooled to −78° C. and was treated dropwise with a solution of N-[2-(3,4-dichlorophenyl) -4-[4-(N-methoxy-N-methylcarbamoyl)piperidino]butyl]-N-methyl-benzamide (400 mg) in tetrahydrofuran (5 mL). The resulting mixture was allowed to warm to room temperature and was stirred for 16 hours. The mixture was cooled to −78° C. and an additional quantity (0.47 mL) of ethylmagnesium chloride was added. The mixture was stirred for 2 hours at −78° C., and was quenched with water and extracted with ethyl acetate. The organic extract was washed sequentially with water and brine, dried, filtered and evaporated to leave a pale yellow syrup. Purification by flash chromatography (95:5:0.1 dichloromethane/methanol/ammonium hydroxide) afforded the title compound as a white foam (217 mg). Treatment of this material (60 mg) with hydrogen chloride (g) in diethyl ether yielded the title compound as a white powder (47 rag), mp 87°–90° C.; NMR: 7.59–7.32 (m, 5), 7.20–6.97 (m,3), 3.84–3.74 (m,2), 3.70–3.48 (m,2), 3.13 (re, 1), 3.05–2.76 (m,4), 3.06,2.75 (2s, NCH$_3$), 2.56 (q,2, J=7.2), 2.25–1.70 (br m, 7), 1.01 (t,3, J=7.2); MS (CI): m/z=477 ((M+i), $^{37}$Cl), 475((M+1), $^{35}$Cl). Analysis for C$_{26}$H$_{32}$Cl$_2$N$_2$O$_2$.1.0 HCl.0.75 H$_{20}$): Calculated: C, 59.43; H, 6.62; N, 5.33; Found: C, 59.50; H, 6.39; N, 5.33.

The starting material N-[2-(3,4-dichlorophenyl)-4-[4-(N-methoxy-N-methyl-carbamoyl) piperidino]butyl]-N-methylbenzamide was prepared as follows.

a. 4-(N-Methoxy-N-methylcarbamoyl)piperidine. A solution of N-methoxy-N-methyl-1-(benzyloxycarbonyl)piperidine-4-carboxamide (2.07 g), prepared as described in Example 1b, in ethanol (45 mL) was hydrogenated over 10% palladium on carbon (207 mg) at a hydrogen pressure of 3.45 bar for 4 hours. The mixture was filtered through diatomaceous earth and evaporated to afford the piperidine as a waxy, white solid (1.21 g); NMR: 3.67 (s,3, OCH$_3$), 3.08 (s,3, NCH$_3$), 2.96 (br m, 2), 2.76 (br m, 1), 2.50 (br m,2), 1.59–1.38 (m, 4); MS (CI): m/z= 173(M+1).

b. N-[2-(3,4-Dichlorophenyl)-4-[4-(N-methoxy-N-methyl-carbamoyl)piperidino] butyl]-H-methylbenzamide. A solution of 4-(N-methoxy-N-methylcarbamoyl)piperidine (500 mg) and N-[2-(3,4-dichlorophenyl)-3-formylpropyl]-N-methylbenzamide (885 mg), prepared as described in Example 1.1., in methanol (25 mL) was adjusted to pH 6 by addition of glacial acetic acid. The resulting mixture was cooled to 0° C. and treated with sodium cyanoborohydride (243 mg). The mixture was stirred for 0.5 hour at 0° C., warmed to room temperature, stirred for 16 hours and evaporated. The residue was dissolved in dichloromethane, washed successively with 1N aqueous sodium hydroxide, water and brine, dried, filtered and evaporated to afford a colorless syrup (1.08 g). Purification by chromatography (93:7:1 dichloromethane/methanol/ammonium hydroxide) afforded N-[2-(3,4-dichlorophenyl)-4-[4-(N-methoxy-N-methylcarbamoyl) piperidino] butyl]-N-methylbenzamidethe as a white foam (653 mg); NMR: 7.56–7.50 (m,4); 7.41–7.28 (m, 4), 4.22 (s,1), 3.56 (s,3), 3.60–3.40 (m,4), 3.20 (s,3), 3.30–3.00 (m,2), 2.50 (re, 1), 2.30 (re, 1), 2.15 (m, 1), 1.97 (m, 2); MS: m/z=451(M).

Example 4. N-[2-(3,4-Dichlorophenyl)-4-[4-(1-hydroxypropyl)piperidino ]butyl]-N-methylbenzamide hydrochloride.

A solution of N-[2-(3,4-dichlorophenyl)-4-[4-(propionyl)piperidino] butyl]-N-methylbenzamide, prepared as described in Example 3, (148 rag) in methanol (10 mL) was cooled to 0° C. and treated with sodium borohydride (13 mg). The resulting mixture was stirred at 0° C for 15 minutes, warmed to room temperature and stirred for 2 hours, and was evaporated. The residue was dissolved in dichloromethane (50 mL) and washed sequentially with water and brine. The organic extract was dried, filtered and evaporated to afford a yellow syrup (176 mg). Purification by chromatography (93:7:0.1 dichloromethane/methanol/ammonium hydroxide) afforded the title compound as a clear syrup (109 mg). Treatment of this material with hydrogen chloride (g) in diethyl ether yielded the the title compound as a white powder (92 rag), mp 95–97.5° C.; NMR: 7.60–7.33 (m, 5), 7.20–6.97 (m,3), 3.84–3.76 (m,2), 3.57–3.48 (br m,2), 3.26 (m,2), 3.23–2.80 (m,4), 3.06,2.76 (2s, NCH$_3$), 2.30–1.78 (br m, 4), 1.68–1.40 (m, 5), 0.96 (t,3, J=7.2); MS (CI): m/z=479((M+1), $^{37}$Cl), 477 ((M+1), $^{35}$Cl). Analysis for C$_{26}$H$_{34}$Cl$_2$N$_2$O$_2$.1.0 HCl.0.75 H$_2$O: Calculated: C, 59.21; H, 6.97; N, 5.31; Found: C, 59.05; H, 6.62; N, 5.62.

Example 5. N-[2-(3,4-Dichlorophenyl)-4-[4-((E)-1-oximinopropyl)piperidino ]butyl]-N-methylbenzamide.

A solution of N-[2-(3,4-dichlorophenyl)-4-[4-(propionyl)piperidino] butyl]-N-methylbenzamide, prepared as described in Example 3, (200 mg), hydroxylamine hydrochloride (44 mg) and pyridine (166 mg) in ethanol (2 mL) was heated to reflux temperature and stirred for 3 hours. Upon cooling to room temperature, a white precipitate formed, which was isolated by filtration, washed with water and dried (150° C./100 mbar) to afford the title compound (137 mg) as a white powder, mp 240°–24.1.5° C. (dec); NMR (CD$_{30}$D): 7.63–7.37 (m,5), 7.23–6.95 (m, 3), 3.88–3.74 (m,2), 3.70–3.45 (m,2), 3.33–3.15 (m, 3), 3.13–2.80 (m, 4), 3.10,2.79 (2s, NCH$_3$), 2.22 (m,3), 2.03 (br m, 4), 1.11 (t,3, J=7.1); MS (CI): m/z=492((M+1), $^{37}$Cl), 490((M+1), $^{35}$Cl). Analysis for C$_{26}$H$_{32}$Cl$_2$N302.2.25 H$_{20}$: Calculated: C, 58.92; H, 6.94; N, 7.93; Found: C, 58.97; H, 6.93; N, 7.89.

Example 6. N-[2-(3,4-Dichlorophenyl)-4-[4-(1-((E)-methoximino)propyl) piperidino]butyl]-N-methylbenzamide hydrochloride.

A solution of N-[2-(3,4-dichlorophenyl)-4-[4-(propionyl)piperidino] butyl]-[-methylbenzamide, prepared as described in Example 3, (128 mg) and methoxylamine hydrochloride (34 mg) in pyridine (6 mL) was heated to reflux temperature and stirred for 6 hours. The mixture was evaporated, the residue suspended in water and extracted with dichloromethane. The organic extract was washed sequentially with water (2×) and brine, dried, filtered and evaporated to leave a tan foam. Purification by chromatography (95:5 dichloromethane/methanol) afforded a clear syrup, which was treated with hydrogen chloride (g) in diethyl ether to yield the title compound as a tan solid (46 mg), mp 83°–85° C.; NMR: 7.61–7.36 (m, 5), 7.21–6.95 (m, 3), 3.83–3.71 (m,2), 3.77 (s, OCH$_3$), 3.70–3.45 (m, 2), 3.29.–2.71 (br m, 5), 3.07,2.76 (2s, NCH$_3$), 2.48–1.72 (br m, 9), 1.06 (t,3, J=7.4); MS (CI): m/z=506((M+1), $^{37}$Cl), 504((M+1), $^{35}$Cl). Analysis for C$_{27}$H$_{35}$Cl$_2$N$_3$O$_2$.1.0 HCl.1.0 H$_2$O: Calculated: C, 58.02; H, 6.85; N, 7.52; Found: C, 58.17; H, 6.51; N, 7.42.

Example 7. N-[2-(3,4-Dichlorophenyl)-4-[4-(1-methyl-1-hydroxyethyl)piperdinobutyl] -N-methylbenzamide hydrochloride.

Using a procedure similar to that described in Example 1, except using 4-(1-methyl-1-hydroxyethyl)piperidine, prepared as described below, and the aldehyde prepared as described in Example 1.1., the title compound was prepared and isolated as a white powder, mp 102°–105° C.; NMR: 7.60–7.56 (m,2), 7.45–7.34 (m,3), 7.21 (m,2), 6.99 (re, 1), 3.84–3.70 (m, 2), 3.58 (m, 2), 3.28 (m, 1), 3.20–2.80 (m,4) 3.07,2.76 (2s, NCH$_3$), 2.20–1.90 (br m, 4), 1.59 (br s,3), 1.18 (s,6); MS (CI): m/z=479((M+1), $^{37}$Cl), 477((M+1), $^{35}$Cl). Analysis for C$_{26}$H$_{34}$Cl$_2$N$_2$O$_2$.1.0 HCl.0.50 H$_2$O: Calculated: C, 59.72; H, 6.94; N, 5.36; Found: C, 59.69; H, 6.87; N, 5.27.

The starting material 4-(1-hydroxy-1-methylethyl)piperidine was prepared as follows.

a. Ethyl 1-(benzyloxycarbonyl)-4-piperidinecarboxylate. A solution of ethyl 4-piperidinecarboxylate (14.71 g) and triethylamine (12.04 g) in chloroform (200 mL) was cooled to 0° C. and treated dropwise with benzyl chloroformate (17.91 g). The resulting mixture was stirred at 0° C. for 1 hour, allowed to warm to room temperature and was stirred for 12 hours. The mixture was washed with 1N hydrochloric acid (3×) and brine, dried, filtered and evaporated to yield a pale yellow oil (26.4 g). This material was purified by chromatography (95:5 dichloromethane/methanol) to afford the amide as a colorless syrup (22.15 g); NMR: 7.35 (m, 5, C6H5), 5.07 (s,2, PhCH2), 4.06 (q,2, J=7.0), 3.91 (br d,2, J=13.3), 2.95 (br,2), 2.53 (m, 1), 1.82 (br d,2, J=13.3), 1.41 (m,2), 1.18 (t,3, J=7.0).

b. 1-(Benzyloxycarbonyl)-4-(1-hydroxy-1-methylethyl)piperidine. A solution of methyllithium (15.32 mL of a 1.4 M solution in diethyl ether) in tetrahydrofuran (15 mL) was cooled to −78° C. and treated dropwise with a solution of ethyl 1-(benzyloxycarbonyl)-4-piperidinecarboxylate (2.50 g) in tetrahydrofuran (10 mL). The resulting solution was stirred at −78° C. for 1 hour, warmed to 0° C. for 1 hour, quenched by addition of 1N hydrochloric acid and extracted with ethyl acetate. The organic extract was washed with 1N hydrochloric acid (2×) and brine, dried, filtered and evaporated to afford a pale yellow oil. Purification by chromatography (90:10 dichloromethane/methanol) gave the alcohol as a clear oil (940 mg); NMR: 7.35 (m,5, $C_6H_5$), 5.05 (s,2, $PhCH_2$), 4.04 (m, 2), 2.69 (br,2), 1.68 (m,2), 1.35–1.03 (m,2), 1.01 (s,6); MS (CI): m/z=278(M+1).

c. 4-(1-Hydroxy-1-methylethyl)piperidine. A solution of 1-(benzyloxycarbonyl)-4-(1-hydroxy-1-methylethyl)piperidine (940 mg) in ethanol (30 mL) was hydrogenolysed over 10% palladium on carbon (100 mg) at a hydrogen pressure of 3.45 bar for 4 hours. The mixture was filtered and evaporated to afford the piperidine as a white foam (430 mg); NMR: 4.49 (s,1, OH), 2.97 (br d,2, J=11.7), 2.40 (m, 2), 1.61 (br d,2, J=12.4), 1.27–1.03 (m,3), 1.00 (s,6).

Example 8. N-[2-(3,4-Dichlorophenyl)-4-[4-(1-ethyl-1-hydroxypropyl)piperidino] butyl]-N-methylbenzamide hydrochloride.

Using a procedure similar to that described in Example 1, except using 4-(1-ethyl-1-hydroxypropyl)piperidine, prepared by a route similar to that described in Example 7, except using ethylmagnesium chloride in place of methyllithium in step b, and the aldehyde prepared as described in Example 1.1., the title compound was isolated as a white solid, mp 102°–104° C.; NMR: 7.59–7.32 (m, 5), 7.20–6.97 (m, 3), 3.83–3.74 (m,2), 3.56 (m, 2), 3.28 (m, 1), 3.25–2.80 (m,4), 3.20,2.75 (2s, $NCH_3$), 2.15 (br s,1), 1.90 (br s,3), 1.67–1.42 (m,7), 0.85 (t,6, J=7.3); MS (CI): m/z=507((M+1), $^{37}Cl$), 505((M+1), $^{35}Cl$). Analysis for $C_{28}H_{38}Cl_2N_2O_2 \cdot 1.0$ HCl·0.75 $H_2O$): Calculated: C, 60.54; H, 7.35; N, 5.04; Found: C, 60.33; H, 7.28; N, 4.98.

Example 9. N-[2-(3,4-Dichlorophenyl)-4-[4-(1-propyl-1-hydroxybutyl)piperidino] butyl]-[-methylbenzamide hydrochloride.

Using a procedure similar to that described in Example 1, except using 4-(1-propyl-1-hydroxybutyl)piperidine, prepared by a route similar to that described in Example 7, except using propylmagnesium chloride in place of methyllithium in step b, and the aldehyde prepared as described in Example 1.1., the title compound was isolated as a white solid; NMR: 7.60–7.32 (m, 5), 7.20–6.97 (m,3), 3.85–3.70 (m,2), 3.60–3.48 (br m, 2), 3.28 (m, 1), 3.25–2.72 (m, 4), 3.07,2.76 (2s, $NCH_3$), 2.17 (br s,1), 1.90 (br s,3), 1.66 (br s,3), 1.45–1.25 (m, 8), 0.92 (t,6, J=7.1); MS (CI): m/z= 535((M+1), $^{37}Cl$), 533((M+1), $^{35}Cl$). Analysis for $C_{30}H_{42}Cl_2N_2O_2 \cdot 1.0$ HCl·0.50 $H_2O$: Calculated: C, 62.23; H, 7.66; N, 4.84; Found: C, 61.98; H, 7.60; N, 4.72.

Example 10. N-[2-(3,4-Dichlorophenyl)-4-[4-(2-acetoxyethyl)piperidino] butyl]-N-methylbenzamide hydrochloride.

Using a procedure similar to that described in Example 1, except using 4-(2-acetoxyethyl)piperidine, prepared as described below, and the aldehyde prepared as described in Example 1.1., the title compound was isolated as a white solid; mp 62°–71° C.; NMR: 7.8–6.9 (br,8), 4.02 (br,1), 1.99 (s,3); MS (CI): m/z=505(M+1). Analysis for $C_{27}H_{34}Cl_2N_2O_3 \cdot HCl \cdot 1.5$ $H_2O$: Calculated: C, 57.00; H, 6.73; N, 4.93; Found: C, 56.85; H, 6.60; N, 5.34.

The starting material 4-(2-acetoxyethyl)piperidine was prepared as follows.

a. 1-(Benzyloxycarbonyl)-4-(2-hydroxyethyl)piperidine. A solution of 4-(2-hydroxyethyl)piperidine (1.29 g) in dichloromethane (30 mL) was treated with triethylamine (1.02 g), cooled to 0° C. and treated dropwise with a solution of benzyl chloroformate (1.706 g) in dichloromethane (10 mL). The reaction mixture was allowed to warm to room temperature, stirred for 1 hour, diluted with dichloromethane (100 mL), and washed successively with 1N hydrochloric acid and brine. The aqueous layers were extracted with dichloromethane. The organic extracts were combined, dried, filtered and evaporated to afford the amide (2.27 g) as a clear amber oil; NMR: 7.35 (m, 5), 5.06 (s,2), 4.71 (t,1, J=6), 4.00 (br,2), 3.42 (m,2), 2.7 (br,2), 1.6–1.0 (m,7); MS (CI): m/z=264(M+1).

b. 1-(Benzyloxycarbonyl)-4-(2-acetoxyethyl)piperidine. A solution of 1-benzyloxycarbonyl-4-(2-hydroxyethyl)piperidine (1.0 g) in dichloromethane (20 mL) was treated with triethylamine (0.38 g), cooled to 0° C. and treated dropwise with a solution acetyl chloride (0.3 g) in dichloromethane (5 mL). The reaction mixture was allowed to warm to room temperature and cooled back to 0° C. Two additional portions of acetyl chloride (0.15 g each) were added and the reaction mixture was allowed to warm to room temperature. The mixture was stirred for 16 hours, diluted with dichloromethane (75 mL) and washed successively with 1N hydrochloric acid and brine. The aqueous washes were extracted with dichloromethane (50 mL). The organic extracts were combined, dried, filtered and evaporated to obtain the acetoxy compound (0.9 g) as a clear oil; NMR: 7.33 (br,5), 5.06 (s,2), 4.0 (br,4), 2.77 (br,2), 1.98 (s,3), 1.62 (d,1, J=13), 1.5–1.6 (m, 4) 0.8–1.2 (m,2); MS (CI): m/z=306(M+1).

c. 4-(2-Acetoxyethyl)piperidine. A solution of 1-(benzyloxycarbonyl)-4-(2-acetoxyethyl)piperidine (0.9 g) in methanol (30 mL) was treated with a solution of anhydrous HCl in ether (1 mL) and was hydrogenated over 10% palladium on carbon at atmospheric pressure for 2 hours. The reaction mixture was filtered through diatomaceous earth and the filtrate was evaporated to afford the piperidine as a solid (0.60 g); NMR (d6-dimethylsulfoxide with trifluoroacetic acid): 4.06 (t,3, J=6.5), 1.92 (s,3); MS (CI): m/z=172(M+1).

Example 11. N-[2-(3,4-Dichlorophenyl)-4-[4-(2-acetamidoethyl)piperidino]butyl]-N-methylbenzamide hydrochloride.

Using a procedure similar to that described in Example 1, except using 4-(2-acetamidoethyl)piperidine, prepared as described below, and the aldehyde prepared as described in Example 1.1., the title compound was isolated as a white solid; NMR: 7.8–6.9 (m,8), 3.30 (s,3), 3.28 (s,3); MS (CI): m/z=504(M+1). Analysis for $C_{27}H_{35}Cl_2N_3O_2 \cdot 1.0$ HCl·1.5 $H_2O$: Calculated: C, 56.65; H, 6.95; N, 7.34; Found: C, 56.62; H, 6.94; N, 7.29.

The starting material 4-(2-acetamidoethyl)piperidine was prepared as follows.

a. 1-(Benzyloxycarbonyl)-4-(2-methanesulfonyloxyethyl)piperidine. A solution of 1-benzyloxycarbonyl-4-(2-hydroxyethyl)piperidine, prepared as described in Example 10a, (0.79 g) in dichloromethane (10 mL) was treated with triethylamine (0.33 cooled to 0° C., and treated with methanesulfonyl chloride (0.34 g). The reaction mixture was allowed to warm to room temperature, stirred for 2 hours, diluted with dichloromethane (50 mL), and washed successively with water and brine. The aqueous washes were extracted with dichloromethane. The combined organic extracts were dried, filtered and evaporated to afford the mesylate (0.97 g) as a clear syrup; NMR: 7.36 (br,5), 5.06 (s,2), 4.24 (t,2, J=6), 4.0 (m, 2), 3.16 (s,3), 2.8 (br,2), 1.5 (br,3), 0.95–1.1 (m,2); MS (FAB): 342(M+1).

b. 1-(Benzyloxycarbonyl)-4-(2-azidoethyl)piperidine. A solution of the 1-(benzyloxycarbonyl)-4-(2-methanesulfonyloxyethyl)piperidine (0.97 g) in N,N-dimethylformamide (15 mL) was treated with sodium azide (0.37 g) and the resulting white suspension was stirred for 16 hours at the room temperature. The reaction mixture was diluted with ethyl acetate (100 mL) and washed with water (4×). The aqueous washes were extracted with ethyl acetate. The organic extracts were combined, dried, filtered and evaporated to afford the crude product (0.7 g). Purification by chromatography (9:1 hexane/ethyl acetate) afforded the azido compound as a clear oil (0.46 g); NMR: 7.35 (m, 5), 5.06 (s,2), 4.01 (m,2), 3.33–3.39 (m, 3), 2.78 (br,2), 1.44–1.67 (m,5), 1.00–1.05 (m, 2); MS (CI): m/z=289(M+1).

c. 1-(Benzyloxycarbonyl)-4-(2-aminoethyl)piperidine. A solution of the 1-(benzyloxycarbonyl)-4-(2-azidoethyl)piperidine (0.46 g) in dry tetrahydrofuran (10 mL) was treated with triphenylphosphine (0.46 g). The resulting solution was stirred at 50° C. for 16 hours, was cooled to the room temperature, treated with aqueous ammonia (4.1 mL) and extracted with diethyl ether (3×). The organic extracts were combined and washed with 1N hydrochloric acid (3×). The combined aqueous extract was washed with ethyl acetate. The aqueous layer was made basic by addition of 50% aqueous sodium hydroxide, and was extracted with dichloromethane (3×). The organic extracts were combined, dried, filtered and evaporated to afford the amide as an oil (0.42 g); NMR: 7.34 (m, 5), 5.06 (s,2), 4.0 (d,2, J=13), 1.62 (d,2, J=13), 1.55 (m, 1), 1.24–1.31 (m,2), 0.95–1.00 (m,2); MS (CI): m/z=263(M+1).

d. 1-(Benzyloxycarbonyl)-4-(2-acetamidoethyl)piperidine. A solution of 1-(benzyloxycarbonyl)-4-(2-aminoethyl)piperidine (0.42 g) in dichloromethane (10 mL) was treated with triethylamine (0.16 g), cooled to 0° C. and treated with acetyl chloride (0.13 g), added in two portions. The reaction mixture was allowed to warm to room temperature and was stirred for 16 hours, was diluted with dichloromethane and washed successively with 1N hydrochloric acid and brine. The organic extract was dried, filtered and evaporated to afford a yellow solid (0.46 g). Purification by chromatography (95:5 dichloromethane:methanol) afforded 1-(benzyloxycarbonyl)-4-(2-acetamidoethyl)piperidine the (0.27 g) as white solid; NMR: 7.8 (br,1), 7.35 (m,5), 5.06 (s,2), 4.00 (d,2, J=13), 3.04 (m,2), 2.7 (br,2), 1.78 (s,3), 1.64 (d,2, J=11), 1.35 (m, 1), 1.32 (m, 2), 0.99 (m,2); MS (CI): m/z=305(M+1).

e. 4-(2-Acetamidoethyl)piperidine. A solution of 1-(benzyloxycarbonyl)-4-(2-acetamidoethyl)piperidine (0.27 g) in methanol (10 mL) was hydrogenolysed over 10% palladium on carbon at atmospheric pressure for 16 hours. The mixture was filtered through diatomaceous earth and the filtrate was evaporated to afford the piperidine (0.13 g); NMR: 7.76 (br,1), 3.02 (m,2), 2.85 (m,2), 2.38 (t,2, J=11), 1.77 (s,3), 1.54 (d,2, J=12), 1.26 (m,2), 0.96 (m,2); MS (CI): m/z=171(M+1).

Example 12. N-[2-(3,4-Dichlorophenyl)-4-[4-(2-hydroxyethyl)piperidino] butyl]-N-methylbenzamide hydrochloride.

Using a procedure similar to that described in Example 1, except using 4-(2-hydroxyethyl)piperidine and the aldehyde prepared as described in Example 1.1., the title compound was isolated as a white solid, mp 45°–52° C.; NMR (CD$_3$OD): 7.54–7.18 (m,7), 6.99 (br,1), 3.83–3.73 (m, 2), 3.63–3.45 (m, 4), 2.76 (s,3), 2.17 (m, 1),2.0–1.9 (m,3), 1.71 (m, 1), 1.52–1.36 (m, 4); MS (CI): m/z=463(M+1). Analysis for C$_{25}$H$_{32}$Cl$_2$N$_2$O$_2$.HCl.1.5 H$_2$O: Calculated: C, 56.99; H, 6.87; N, 5.32; Found: C, 56.72; H, 6.31; N, 5.23.

Example 13. (S)-N-[2-(3,4-Dichlorophenyl)-4-(4-propionylpiperidino)butyl] -N-methylbenzamide hydrochloride.

Using a procedure similar to that described in Example 3, except using (S)-N-[2-(3,4-dichlorophenyl)-4-[4-(N-methoxy-N-methylcarbamoyl) piperidino]butyl]-N-methylbenzamide, the title compound was isolated as a white solid, mp 85°–90° C.; NMR: 7.60–7.34 (m,5), 7.20–6.98 (m,3), 3.85–3.72 (m,2), 3.70–3.48 (m,2), 3.26 (m, 1), 3.20–2.77 (m, 4), 3.07,2.76 (2,s, NCH$_3$), 2.57 (q,2, J=7.1), 2.25–1.70 (br m,7), 1.02 (t,3, J=7.2); MS (CI): m/z=477((M+1), $^{37}$Cl), 475((M+1), $^{35}$Cl). Analysis for C$_{26}$H$_{32}$Cl$_2$N$_2$O$_2$.1.0 HCl.0.75 H$_2$O: Calculated: C, 59.43; H, 6.62; N, 5.33; Found: C, 59.58; H, 6.33; N, 5.17.

The starting material (S)-N-[2-(3,4-dichlorophenyl)-4-[4-(N-methoxy-N-methylcarbamoyl) piperidino]butyl]-N-methylbenzamide was prepared as follows.

a. 2-(3,4-Dichlorophenyl)-4-hydroxybutylamine. A solution of 2-(3,4-dichlorophenyl)-4-(2-tetrahydropyranyloxy)butylamine (550 g), prepared as described in Example 1.h., in methanol (3.3 L) was treated with 6N hydrochloric acid (352 mL). The reaction mixture was stirred for 3 hours and evaporated. The residue was dissolved in water (3 L) and extracted with diethyl ether. The aqueous solution was made basic by addition of sodium hydroxide, and extracted with ethyl acetate (4×). The organic extracts were combined, washed with brine, dried and evaporated to afford the alcohol as a waxy yellow solid (367 g); NMR (CDCl$_3$): 7.38 (d,1, J=8.3), 7.28 (d, 1, J=2.1); 7.03 (dd, 1, J=2.1, 8.3), 3.66 (br,1), 3.52 (br,1), 3.1–2.3 (br,5), 1.91 (br,2).

b. (S)-2-(3,4-Dichlorophenyl)-4-hydroxybutylamine. A solution of D-tartaric acid (77.85 g) in methanol (2 L) was heated to reflux temperature and was treated with a solution of 2-(3,4-dichlorophenyl)-4-hydroxybutylamine (120.0 g) in methanol (0.8 L). The resulting mixture was stirred at reflux for 0.5 hour and was allowed to slowly cool to room temperature. The crystals which formed on standing (60.8 g) were isolated by filtration and dried. Concentration of the mother liquor to ca. 1 L afforded an additional quantity of salt (12.3 g), which was isolated by filtration and dried. The combined tartrate salt (73.1 g) was recrystallized from methanol (3.7 L), to afford the optically enriched salt (49.85 g). The salt was suspended in water (200 mL), treated with 1N aqueous sodium hydroxide (500 mL) and extracted with dichloromethane (5×). The dichloromethane extracts were combined, washed with brine, dried, filtered and evaporated to afford the optically enriched alcohol (30.6 g) as a waxy white solid; NMR (CD$_3$OD): 7.46 (d,1, J=8.3), 7.42 (d,1, J=2.1), 7.18 (dd,1, J=2.1, 8.3), 4.84 (brs,2), 3.50–3.30 (m, 2), 2.87–2.78 (m, 3), 1.93 (m, 1), 1.73 (m, 1); MS (CI): m/z=238((M+1), $^{37}$Cl $^{37}$Cl), 236((M+1), $^{37}$Cl $^{35}$Cl), 234((M+1), $^{35}$Cl $^{35}$Cl).

c. Ethyl (S)-N-[2-(3,4-dichlorophenyl)-4-hydroxybutyl]carbamate. A solution of (S)-2-(3,4-dichlorophenyl)-4-hydroxybutylamine (30.4 g) and triethylamine (15.2 g) in dichloromethane (400 mL) was cooled to −25° C. and treated dropwise with a solution of ethyl chloroformate (15.2 g) in dichloromethane (400 mL). The mixture was allowed to warm to room temperature and stirred for 16 hours. The reaction was washed with 1N hydrochloric acid, 10% aqueous sodium bicarbonate and brine, dried, filtered and evaporated to afford an amber syrup. Purification by chromatography (1:1 dichloromethane:ethyl acetate) gave the amide (28.95 g) as a light yellow oil; NMR (CDCl$_3$): 7.42 (d,1, J=8.3), 7.29 (d, 1, J=2.1), 7.05 (dd,1, J=2.1, 8.3), 4.74 (br,1), 4.10 (m, 2); 3.65–3.46 (m, 3), 3.25 (m, 1), 2.98 (m, 1), 1.89 (m, 1), 1.76 (m, 1), 1.23 (m,3); MS (CI): m/z=310((M+1), $^{37}$Cl $^{37}$Cl), 308((M+1), $^{37}$Cl $^{35}$Cl), 306((M+1), $^{35}$Cl $^{35}$Cl).

d. (S)-N-[2-(3,4-Dichlorophenyl)-4-hydroxybutyl]-N-methylamine. A solution of ethyl (S)-N-[2-(3,4-dichlorophenyl)-4-hydroxybutyl] carbamate (28.9 g) in tetrahydrofuran (200 mL) was added dropwise to a suspension of lithium aluminum hydride (7.3 g) in tetrahydrofuran (100 mL). The reaction mixture was heated to reflux for 2 hours, cooled to 0° C., and quenched by dropwise addition of saturated aqueous sodium sulfate solution (25 mL). The suspension was filtered through diatomaceous earth, the filter cake washed with tetrahydrofuran (6×) and the filtrate evaporated to yield (S)-N-[2-(3,4-dichlorophenyl)-4-hydroxybutyl]-N-methylamine (24.0 g) as a pale yellow oil; NMR (CDCl$_3$): 7.38 (d,1, J=8.3), 7.27 (d, 1, J=2.1), 7.02 (dd,1, J=2.1, 8.3), 3.71 (m, 1), 3.53 (m, 1), 2.82–2.72 (m, 3), 2.45 (s,3), 1.88 (m, 2); MS (CI): m/z=252((M+1), $^{37}$Cl $^{37}$Cl), 250((M+1), $^{37}$Cl $^{35}$Cl), 248((M+1), $^{35}$Cl $^{35}$Cl).

e. (S)-N-[2-(3,4-Dichlorophenyl)-4-hydroxybutyl]-N-methylbenzamide. A solution of (S)-N-[2-(3,4-dichlorophenyl)-4-hydroxybutyl] -N-methylamine (24.0 g) and triethylamine (25.0 g) in dichloromethane (400 mL) was cooled to 0° C. and was treated dropwise with a solution benzoyl chloride (14.05 g) in dichloromethane (100 mL). The mixture was allowed to warm to room temperature, stirred for 16 hours, washed (1N hydrochloric acid (2×), saturated aqueous sodium bicarbonate (2×), and brine), dried, filtered and evaporated to leave a clear oil which solidified on standing. Purification by chromatography (dichloromethane; 99:1 dichloromethane:methanol; 97.5:2.5 dichloromethane:methanol) afforded the benzamide (20.24 g) as a white powder; mp 123°–125° C.; [α]$_D$=−18.7 (c=2.03, MeOH); NMR (CD$_3$OD): 7.53–6.90 (m, 8), 3.84 (m, 1), 3.69 (m, 1), 3.51 (m, 1), 3.42–3.23 (m, 2), 3.05–2.77 (2s,3), 1.9–1.6 (m,2); MS (CI): m/z= 356((M+1), $^{37}$Cl $^{37}$Cl), 354((M+1), $^{37}$Cl $^{35}$Cl), 352((M+1), $^{35}$Cl $^{35}$Cl).

f. (S)-N-[2-(3,4-Dichlorophenyl)-3-formylpropyl]-N-methylbenzamide. Using a procedure similar to that described in Example 1.1., except using (S)-N-[2-(3,4-dichlorophenyl)-4-hydroxybutyl] -N-methylbenzamide, the aldehyde was isolated as a pale amber syrup; MS (CI): m/z= 352((M+1), $^{37}$Cl), 350((M+1), $^{35}$Cl).

g. (S)-N-[2-(3,4-Dichlorophenyl)-4-[4-(N-methoxy-N-methylcarbamoyl)piperidino] butyl]-N-methylbenzamide. Using a procedure similar to that described in Example 3.b., except using (S)-N-[2-(3,4-dichlorophenyl)-3-propyl]-N-methylbenzamide as the aldehyde component in the reductive alkylation, (S)-N-[2-(3,4-dichlorophenyl)-4-[4-(N-methoxy-N-methylcarbamoyl)piperidino] butyl]-N-methylbenzamide was isolated as a white foam; NMR: 7.56–7.50 (m, 4); 7.41–7.28 (m, 4), 4.22 (s,1), 3.56 (s,3), 3.60–3.40 (m, 4), 3.20 (s,3), 3.30–3.00 (m,2), 2.50 (m, 1), 2.30 (m, 1), 2.15 (m, 1), 1.97 (m,2); MS: m/z=451(M).

Example 14. (S)-N-[2-(3,4-Dichlorophenyl)-4-[4-((Z)-1-oximinopropyl)piperidino] butyl]-N-methylbenzamide hydrochloride.

A solution of (S)-N-[2-(3,4-dichlorophenyl)-4-(4-propionylpiperidino)butyl] -N-methylbenzamide (485 mg), hydroxylamine hydrochloride (142 mg) and sodium acetate (167 mg) in acetic acid (8 mL) was stirred for 1 hour at room temperature, was diluted with water (20 mL) and neutralized to pH 7 by addition of sodium bicarbonate. The resulting mixture was extracted with diethyl ether (3×). The organic extracts were combined, washed successively with saturated aqueous sodium bicarbonate and brine, dried, filtered and evaporated to leave a white foam (496 mg). Purification by chromatography (65:35:10:0.5 dichloromethane:acetone:methanol:ammonium hydroxide) afforded the Z oxime isomer (R$_f$=0.61) as a white foam (97 mg). Treatment of this product with hydrogen chloride (g) in diethyl ether yielded the title compound as a white solid, mp 152°–155° C.; NMR: 7.62–7.56 (m, 2), 7.43–7.33 (br m, 3), 7.23–6.97 (br m, 3), 3.85–3.74 (m,2), 3.70–3.45 (m, 2), 3.28 (m, 1), 3.13–2.80 (m, 4), 3.07,2.77 (2s, NCH$_3$), 2.34 (m,2), 2.23–1.75 (br m, 4), 1.09 (m,3); MS (CI): m/z=492((M+1), $^{37}$Cl), 490((M+1), $^{35}$Cl). Analysis for C$_{26}$H$_{32}$Cl$_2$N$_3$O$_2$·1.0 HCl·0.75 H$_2$O: Calculated: C, 57.78; H, 6.62; N, 7.79; Found: C, 57.77; H, 6.40; N, 7.75.

Example 15. (S)-N-[2-(3,4-Dichlorophenyl)-4-[4-((E)-1-oximinopropyl)piperidino] butyl]-N-methylbenzamide hydrochloride.

From the chromatographic purification in Example 14, a second fraction (Rf=0.53) was isolated, which afforded the E oxime isomer as a white foam (172 mg). Treatment of this product with hydrogen chloride (g) in diethyl ether yielded the title compound as a white solid, mp 127°–130° C.; NMR: 7.58 (m,2), 7.42–7.31 (br m,3), 7.19–6.95 (br m, 3), 3.85–3.74 (m,2), 3.70–3.45 (m,2), 3.24 (m, 1), 3.19–2.75 (m, 4), 3.04,2.73 (2s, NCH$_3$), 2.30 (q,2, J=7.6), 2.19–1.68 (br m,4), 1.05 (t,3, J=7.6); MS (CI): m/z=492((M+1), $^{37}$Cl), 490((M+1), $^{35}$Cl). Analysis for C$_{26}$H$_{32}$Cl$_2$N$_3$O$_2$·1.0 HCl·0.25 H$_2$O: Calculated: C, 58.87; H, 6.37; N, 7.92; Found: C, 58.81; H, 6.48; N, 7.83.

Example 16. (S)-N-[2-(3,4-Dichlorophenyl)-4-[4-(1-ethyl-1-hydroxypropyl)piperidino] butyl]-N-methylbenzamide hydrochloride.

Using a procedure similar to that described in Example 1, except using 4-(1-ethyl-1-hydroxypropyl)piperidine), prepared as described in Example 8, and the (S)-aldehyde, prepared as described in Example 13f., the title compound was isolated as an off white powder, mp 103°–105° C.; NMR: 7.61–7.30 (br m, 5), 7.20–6.93 (br m,3), 3.86–3.70 (m,2), 3.56 (m,2), 3.25 (m, 1), 3.20–2.76 (m,4), 3.05,2.74 (2s, NCH$_3$), 2.15 (brs,1), 1.90 (brs,3), 1.71–1.38 (m,7), 0.85 (t,6, J=7.3); MS (CI): m/z=507((M+1), $^{37}$Cl), 505((M+1), $^{35}$Cl). Analysis for C$_{28}$H$_{38}$Cl$_2$N$_2$O$_2$·1.0 HCl·0.50 H$_2$O: Calculated: C, 61.04; H, 7.32; N, 5.08; Found: C, 61.18; H, 7.33; N, 5.06.

Example 17. N-[2-(3,4-Dichlorophenyl)-4-(4-propylpiperidino)butyl]-N-methylbenzamide hydrochloride.

Using a procedure similar to that described in Example 1, except substituting 4-propylpiperidine for the 4-(1-hydroxyethyl)piperidine used therein, the title compound was prepared. Chromatography with dichloromethane:methanol followed by conversion to the hydrochloride salt gave a white solid; mp 73°–87° C.; NMR (CD$_3$OD): 0.9 (t,3, J=7), 1.2–1.6 (m,7), 1.7–2.3 (m,4), 2.5–3.4 (m,8), 3.4–3.6 (m,2), 3.6–3.8 (m,2), 6.8–7.2 (m,3), 7.3–7.4 (m,3), 7.4–7.6 (m,2); MS (CI): m/z=461(M+1). Analysis for: C$_{26}$H$_{34}$Cl$_2$N$_2$O·1.0 HCl·0.5 H$_2$O: Calculated: C, 61.60; H, 7.16; N, 5.53; Found: C, 61.31; H, 6.96; N, 5.52.

Example 18. N-[2-(3,4-Dichlorophenyl)-4-(4-ethoxycarbonylpiperidino)butyl] -N-methylbenzamide hydrochloride.

Using a procedure similar to that described in Example 1 except substituting 4-ethoxycarbonylpiperidine for the 4-(1-hydroxyethyl)piperidine used therein, the title compound was prepared. Chromatography with dichloromethane:methanol as the eluent, followed by conversion to the hydrochloride salt gave a white solid; mp 48–65; NMR (CD₃OD): 1.1–1.2 (m,3), 1.8–2.2 (m,7), 2.4–3.8 (m,12), 4.0–4.1 (q,J=7,2), 6.8–7.2 (m,2), 7.2–7.4 (s,4), 7.4–7.8 (m,2) 10.6 (br,1); MS: m/z=491(M+1); Analysis for: $C_{26}H_{32}Cl_2N_2O_3 \cdot 1.0$ HCl$\cdot 1.0$ H₂O: Calculated: C, 57.20; H, 6.46; N, 5.13; Found: C, 56.93; H, 6.17; N, 5.06.

Example 19. The following illustrates representative pharmaceutical dosages forms which may be used for the therapeutic or prophylactic administration of a compound of formula I, or a pharmaceutically acceptable salt thereof, (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
|  | 300.0 |
| (ii) Tablet 2 | mg/tablet |
| 'Compound X' | 20.0 |
| Microcrystalline cellulose | 410.0 |
| Starch | 50.0 |
| Sodium starch glycolate | 15.0 |
| Magnesium stearate | 5.0 |
|  | 500.0 |
| (iii) Capsule | mg/capsule |
| 'Compound X' | 10.0 |
| Colloidal silicon dioxide | 1.5 |
| Lactose | 465.5 |
| Pregelatinized starch | 120.0 |
| Magnesium stearate | 3.0 |
|  | 600.0 |
| (iv) Aerosol | mg/can |
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

It will be appreciated that the above pharmaceutical compositions may be varied according to well-known pharmaceutical techniques to accomodate differing amounts and types of active ingredient 'Compound X'. The aerosol (iv) may be used in conjunction with a standard, metered dose aerosol dispenser.

Formulae

I

II

III

IV

V

IIa

Scheme I.

VI

VII

VIII

25
-continued
Scheme I.

VII →  X (S)-X

26
-continued
Scheme II.

(S)-IV ← (S)-IX (S)-III

---

What is claimed is:

1. A compound of formula I wherein

Q is phenyl which may bear one or two substituents independently selected from halo, trifluoromethyl, hydroxy, (1–3C)alkoxy, (1–3C)alkyl and methylenedioxy; or Q is thienyl, imidazolyl, benzothiophenyl or naphthyl any of which may bear a halo substituent; or Q is biphenylyl; or Q is carbon-linked indolyl which may bear a benzyl substituent at the 1-position;

$Q^1$ is hydrogen or (1–3C)alkyl;

$Q^2$ is aryl or heteroaryl, which aryl or heteroaryl radical may optionally bear a substituent independently selected from halo, hydroxy, (1–4C)alkoxy or (1–4C)alkyl;

R is (1–8C)alkyl, which is substituted at the carbon attached to the piperidine ring by a substitutent selected from hydroxy, lower alkoxy and lower acyloxy.

2. A compound of formula I as claimed in claim 1 in which Q is 3,4-dichlorophenyl, $Q^1$ is hydrogen and $Q^2$ is phenyl, or a pharmaceutically acceptable salt thereof.

3. A compound of formula I as claimed in claim 1 in which Q is 3,4-dichlorophenyl; $Q^1$ is hydrogen; $Q^2$ is phenyl; (1–8C)alkyl is ethyl, propyl, butyl, pentyl, isopropyl, 3-pentyl or 4-heptyl.

4. A compound of formula I as claimed in claim 1, wherein R is 1-hydroxyethyl, 1-hydroxypropyl, 1-hydroxybutyl, 1-hydroxy-1-methylethyl, 1-ethyl-1-hydroxy-propyl, and 1-hydroxy-1-propylbutyl; or a pharmaceutically acceptable salt thereof.

5. A compound of formula I as claimed in claim 1 which is (S)-N-[2-(3,4-dichlorophenyl )-4-[4-(1-ethyl-1-hydroxypropyl)piperidino] butyl]-N-methylbenzamide, or a pharmaceutically acceptable salt thereof.

6. A salt as claimed in claims 1 which is made with an acid which provides a physiologically acceptable anion.

7. A pharmaceutical composition comprising a pharmaceutically acceptable diluent or carrier and a compound of formula I, or a pharmaceutically acceptable salt thereof, as claimed in claim 1.

8. A method for the treatment of asthma comprising administering to a human or other manual in need thereof an effective amount of a compound of formula I, or a pharmaceutically acceptable salt thereof, as claimed in claim 1.

* * * * *

UNITED STATES PATENT AND TRADEMARK OFFICE
CERTIFICATE OF CORRECTION

PATENT NO. : 5,521,199

DATED : May 28, 1996

INVENTOR(S) : Jacobs et al.

It is certified that error appears in the above-indentified patent and that said Letters Patent is hereby corrected as shown below:

Column 27, line 25, "from hydroxy, lower alkoxy and lower acyloxy." should read --from hydroxy, lower alkoxy and lower acyloxy, or a pharmaceutically acceptable salt thereof.--.

Column 28, line 24, "administering to a human or other manual in need thereof an" should read --administering to a human or other mammal in need thereof an--.

Signed and Sealed this

Third Day of September, 1996

Attest:

BRUCE LEHMAN

*Attesting Officer*     *Commissioner of Patents and Trademarks*